(12) United States Patent
Salahieh et al.

(10) Patent No.: US 9,358,106 B2
(45) Date of Patent: *Jun. 7, 2016

(54) METHODS AND APPARATUS FOR PERFORMING VALVULOPLASTY

(71) Applicant: BOSTON SCIENTIFIC SCIMED, INC., Maple Grove, MN (US)

(72) Inventors: Amr Salahieh, Saratoga, CA (US); Dwight P. Morejohn, Davis, CA (US); Daniel K. Hildebrand, San Francisco, CA (US); Tom Saul, El Granada, CA (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/076,846

(22) Filed: Nov. 11, 2013

(65) Prior Publication Data

US 2014/0135912 A1 May 15, 2014

Related U.S. Application Data

(63) Continuation of application No. 11/314,969, filed on Dec. 20, 2005, now Pat. No. 8,579,962, and a continuation-in-part of application No. 10/982,692, filed on Nov. 5, 2004, now Pat. No. 7,824,442, which is a continuation-in-part of application No. 10/746,120, filed on Dec. 23, 2003, now abandoned.

(60) Provisional application No. 60/724,455, filed on Oct. 6, 2005.

(51) Int. Cl.
*A61F 2/24* (2006.01)
*A61B 17/00* (2006.01)
*A61F 2/95* (2013.01)

(52) U.S. Cl.
CPC ............. *A61F 2/2412* (2013.01); *A61F 2/2418* (2013.01); *A61F 2/2439* (2013.01); *A61B 2017/00783* (2013.01); *A61F 2002/9517* (2013.01); *A61F 2250/0097* (2013.01)

(58) Field of Classification Search
CPC ................... A61B 2017/00783; A61B 2/2439; A61B 2002/9511; A61F 2/2418; A61F 2/2439; A61F 2/90; A61F 2/24; A61F 2/2412
See application file for complete search history.

(56) References Cited

U.S. PATENT DOCUMENTS 15,192 A 6/1856 Peale
2,682,057 A 6/1954 Lord
(Continued)

FOREIGN PATENT DOCUMENTS

CN 1338951 A 3/2002
DE 19532846 3/1997
(Continued)

OTHER PUBLICATIONS

Examiner's First Report on AU Patent Application No. 2011202667, issued on May 17, 2012.
(Continued)

*Primary Examiner* — Alexander Orkin
(74) *Attorney, Agent, or Firm* — Seager, Tufte & Wickhem LLP

(57) ABSTRACT

The present invention relates to apparatus and methods for performing valvuloplasty. In some embodiments, the apparatus includes an expandable braid valvuloplasty device. In some embodiments, the methods and apparatus may be used as an adjunct to percutaneous heart valve replacement. In some embodiments, the apparatus and methods may provide a medical practitioner with feedback, monitoring or measurement information, e.g., information relevant to percutaneous transcatheter heart valve replacement.

12 Claims, 14 Drawing Sheets

(56) References Cited

U.S. PATENT DOCUMENTS

| | | |
|---|---|---|
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head |
| 3,143,742 A | 8/1964 | Cromie |
| 3,334,629 A | 8/1967 | Cohn |
| 3,367,364 A | 2/1968 | Cruz |
| 3,409,013 A | 11/1968 | Berry |
| 3,445,916 A | 5/1969 | Schulte |
| 3,540,431 A | 11/1970 | Mobin-Uddin |
| 3,548,417 A | 12/1970 | Kischer |
| 3,570,014 A | 3/1971 | Hancock |
| 3,587,115 A | 6/1971 | Shiley |
| 3,592,184 A | 7/1971 | Watkins |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell |
| 4,056,854 A | 11/1977 | Boretos et al. |
| 4,106,126 A | 8/1978 | Traenkle |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis |
| 4,323,358 A | 4/1982 | Lentz |
| 4,326,306 A | 4/1982 | Poler |
| 4,339,831 A | 7/1982 | Johnson |
| 4,343,048 A | 8/1982 | Ross |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno |
| 4,501,030 A | 2/1985 | Lane |
| 4,531,943 A | 7/1985 | Van Tassel |
| 4,535,483 A | 8/1985 | Klawitter |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,680,031 A | 7/1987 | Alonso |
| 4,692,164 A | 9/1987 | Dzemeshkevich |
| 4,705,516 A | 11/1987 | Barone |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann |
| 4,883,458 A | 11/1989 | Shiber |
| 4,885,005 A | 12/1989 | Nashef |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth |
| 5,152,771 A | 10/1992 | Sabbaghian |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef |
| 5,217,481 A | 6/1993 | Barbara |
| 5,217,483 A | 6/1993 | Tower |
| 5,258,023 A | 11/1993 | Reger |
| 5,258,042 A | 11/1993 | Mehta |
| 5,282,847 A | 2/1994 | Trescony |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,464,449 A * | 11/1995 | Ryan et al. .................. 623/1.23 |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney |

(56) References Cited

U.S. PATENT DOCUMENTS

| | | | |
|---|---|---|---|
| 5,571,215 A | 11/1996 | Sterman et al. |
| 5,573,520 A | 11/1996 | Schwartz |
| 5,575,818 A | 11/1996 | Pinchuk |
| 5,591,185 A | 1/1997 | Kilmer |
| 5,591,195 A | 1/1997 | Taheri |
| 5,607,464 A | 3/1997 | Trescony |
| 5,609,626 A | 3/1997 | Quijano |
| 5,645,559 A | 7/1997 | Hachtman et al. |
| 5,653,684 A * | 8/1997 | Laptewicz et al. ............... 604/22 |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries |
| 5,695,498 A | 12/1997 | Tower |
| 5,709,713 A | 1/1998 | Evans |
| 5,713,951 A | 2/1998 | Garrison |
| 5,713,953 A | 2/1998 | Vallana et al. |
| 5,716,370 A | 2/1998 | Williamson, IV et al. |
| 5,716,417 A | 2/1998 | Girard |
| 5,720,391 A | 2/1998 | Dohm et al. |
| 5,725,549 A | 3/1998 | Lam |
| 5,728,068 A | 3/1998 | Leone |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein |
| 5,769,812 A | 6/1998 | Stevens et al. |
| 5,800,456 A | 9/1998 | Maeda et al. |
| 5,800,531 A | 9/1998 | Cosgrove |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,051,104 A | 4/2000 | Oriaran et al. |
| 6,059,827 A | 5/2000 | Fenton |
| 6,074,418 A | 6/2000 | Buchanan |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley |
| 6,179,859 B1 | 1/2001 | Bates |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian |
| 6,302,906 B1 | 10/2001 | Goicoechea |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | De Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsuigita et al. |
| 6,540,768 B1 | 4/2003 | Diaz et al. |
| 6,562,058 B2 | 5/2003 | Seguin et al. |

(56) References Cited

U.S. PATENT DOCUMENTS

| | | |
|---|---|---|
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,769,434 B2 | 8/2004 | Liddicoat |
| 6,773,454 B2 | 8/2004 | Wholey et al. |
| 6,776,791 B1 | 8/2004 | Stallings et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Hyodoh et al. |
| 6,797,002 B2 | 9/2004 | Spence |
| 6,814,746 B2 | 11/2004 | Thompson et al. |
| 6,821,297 B2 | 11/2004 | Snyders |
| 6,824,041 B2 | 11/2004 | Grieder |
| 6,830,585 B1 | 12/2004 | Artof |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph |
| 6,866,650 B2 | 3/2005 | Stevens |
| 6,866,669 B2 | 3/2005 | Buzzard et al. |
| 6,872,223 B2 | 3/2005 | Roberts |
| 6,872,226 B2 | 3/2005 | Cali |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri et al. |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,979,350 B2 | 12/2005 | Moll et al. |
| 6,984,242 B2 | 1/2006 | Campbell et al. |
| 6,989,027 B2 | 1/2006 | Allen |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano |
| 7,097,658 B2 | 8/2006 | Oktay |
| 7,122,020 B2 | 10/2006 | Mogul |
| 7,125,418 B2 | 10/2006 | Duran |
| 7,141,063 B2 | 11/2006 | White et al. |
| 7,166,097 B2 | 1/2007 | Barbut |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,258,696 B2 | 8/2007 | Rabkin et al. |
| 7,267,686 B2 | 9/2007 | DiMatteo |
| 7,276,078 B2 | 10/2007 | Spenser |
| 7,322,932 B2 | 1/2008 | Xie |
| 7,326,236 B2 | 2/2008 | Andreas et al. |
| 7,329,279 B2 | 2/2008 | Haug |
| 7,374,560 B2 | 5/2008 | Ressemann et al. |
| 7,381,219 B2 | 6/2008 | Salahieh |
| 7,381,220 B2 | 6/2008 | Macoviak |
| 7,399,315 B2 | 7/2008 | Iobbi |
| 7,445,631 B2 | 11/2008 | Salahieh |
| 7,470,285 B2 | 12/2008 | Nugent |
| 7,473,417 B2 | 1/2009 | Zeltinger et al. |
| 7,491,232 B2 | 2/2009 | Bolduc et al. |
| 7,510,574 B2 | 3/2009 | Le |
| 7,524,330 B2 | 4/2009 | Berreklouw |
| 7,530,995 B2 | 5/2009 | Quijano |
| 7,544,206 B2 | 6/2009 | Cohn |
| 7,601,159 B2 | 10/2009 | Ewers et al. |
| 7,622,276 B2 | 11/2009 | Cunanan |
| 7,628,802 B2 | 12/2009 | White et al. |
| 7,628,803 B2 | 12/2009 | Pavcnik |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,736,388 B2 | 6/2010 | Goldfarb et al. |
| 7,748,389 B2 | 7/2010 | Salahieh |
| 7,758,625 B2 | 7/2010 | Wu et al. |
| 7,780,725 B2 | 8/2010 | Haug |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin, Jr. |
| 7,846,204 B2 | 12/2010 | Letac |
| 7,857,845 B2 | 12/2010 | Stacchino et al. |

(56) References Cited

U.S. PATENT DOCUMENTS

| | | |
|---|---|---|
| 7,892,292 B2 | 2/2011 | Stack et al. |
| 7,914,574 B2 | 3/2011 | Schmid et al. |
| 7,918,880 B2 | 4/2011 | Austin |
| 7,927,363 B2 | 4/2011 | Perouse |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,512,394 B2 | 8/2013 | Schmid et al. |
| 8,579,962 B2 | 11/2013 | Salahieh et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,992,608 B2 * | 3/2015 | Haug et al. .................. 623/2.38 |
| 2001/0002445 A1 | 5/2001 | Vesely |
| 2001/0007956 A1 | 7/2001 | Letac et al. |
| 2001/0010017 A1 | 7/2001 | Letac |
| 2001/0021872 A1 | 9/2001 | Bailey |
| 2001/0025196 A1 | 9/2001 | Chinn |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Don Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence |
| 2002/0032481 A1 | 3/2002 | Gabbay |
| 2002/0042651 A1 | 4/2002 | Liddicoat |
| 2002/0052651 A1 | 5/2002 | Myers |
| 2002/0055767 A1 | 5/2002 | Forde |
| 2002/0055769 A1 | 5/2002 | Wang |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111665 A1 * | 8/2002 | Lauterjung .................. 623/1.1 |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle |
| 2002/0177766 A1 | 11/2002 | Mogul |
| 2002/0183781 A1 | 12/2002 | Casey |
| 2002/0188341 A1 | 12/2002 | Elliott |
| 2002/0188344 A1 | 12/2002 | Bolea et al. |
| 2002/0193871 A1 | 12/2002 | Beyersdorf |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams |
| 2003/0069646 A1 | 4/2003 | Stinson |
| 2003/0070944 A1 | 4/2003 | Nigam |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh |
| 2003/0149476 A1 | 8/2003 | Damm et al. |
| 2003/0149478 A1 | 8/2003 | Figulla et al. |
| 2003/0153974 A1 | 8/2003 | Spenser |
| 2003/0165352 A1 | 9/2003 | Ibrahim |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin |
| 2004/0097788 A1 | 5/2004 | Mourlas |
| 2004/0098022 A1 | 5/2004 | Barone |

(56) References Cited

U.S. PATENT DOCUMENTS

| | | |
|---|---|---|
| 2004/0098098 A1 | 5/2004 | McGuckin, Jr. |
| 2004/0098099 A1 | 5/2004 | McCullagh et al. |
| 2004/0098112 A1 | 5/2004 | DiMatteo |
| 2004/0107004 A1 | 6/2004 | Levine |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0117009 A1 | 6/2004 | Cali |
| 2004/0122468 A1 | 6/2004 | Yodfat et al. |
| 2004/0122516 A1 | 6/2004 | Fogarty |
| 2004/0127936 A1 | 7/2004 | Salahieh |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin |
| 2004/0210306 A1 | 10/2004 | Quijano |
| 2004/0210307 A1 | 10/2004 | Khairkhahan |
| 2004/0215331 A1 | 10/2004 | Chew et al. |
| 2004/0215333 A1 | 10/2004 | Duran |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. |
| 2004/0225354 A1 | 11/2004 | Allen |
| 2004/0225355 A1 | 11/2004 | Stevens |
| 2004/0243221 A1 | 12/2004 | Fawzi |
| 2004/0254636 A1 | 12/2004 | Flagle et al. |
| 2004/0260390 A1 | 12/2004 | Sarac |
| 2005/0008589 A1 | 1/2005 | Legrand |
| 2005/0010287 A1 | 1/2005 | Macoviak |
| 2005/0021136 A1 | 1/2005 | Xie |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat |
| 2005/0060016 A1 | 3/2005 | Wu et al. |
| 2005/0060029 A1 | 3/2005 | Le |
| 2005/0065594 A1 | 3/2005 | DiMatteo |
| 2005/0075584 A1 | 4/2005 | Cali |
| 2005/0075662 A1 | 4/2005 | Pedersen et al. |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075730 A1 | 4/2005 | Myers |
| 2005/0075731 A1 | 4/2005 | Artof |
| 2005/0084595 A1 | 4/2005 | Shukla |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster |
| 2005/0203615 A1 | 9/2005 | Forster |
| 2005/0203616 A1 | 9/2005 | Cribier |
| 2005/0203617 A1 | 9/2005 | Forster et al. |
| 2005/0203618 A1 | 9/2005 | Sharkawy |
| 2005/0203818 A9 | 9/2005 | Rotman |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh |
| 2006/0195183 A1 | 8/2006 | Navia et al. |
| 2006/0253191 A1 | 11/2006 | Salahieh |
| 2006/0259134 A1 | 11/2006 | Schwammenthal et al. |
| 2006/0271166 A1 | 11/2006 | Thill et al. |
| 2006/0287668 A1 | 12/2006 | Fawzi |
| 2006/0287717 A1 | 12/2006 | Rowe et al. |
| 2007/0010876 A1 | 1/2007 | Salahieh |
| 2007/0010877 A1 | 1/2007 | Salahieh |
| 2007/0016286 A1 | 1/2007 | Herrmann et al. |
| 2007/0055340 A1 | 3/2007 | Pryor |
| 2007/0061008 A1 | 3/2007 | Salahieh |
| 2007/0088431 A1 | 4/2007 | Bourang et al. |
| 2007/0100427 A1 | 5/2007 | Perouse |
| 2007/0112355 A1 | 5/2007 | Salahieh |
| 2007/0118214 A1 | 5/2007 | Salahieh |
| 2007/0162107 A1 | 7/2007 | Haug |
| 2007/0173918 A1 | 7/2007 | Dreher |
| 2007/0203503 A1 | 8/2007 | Salahieh |
| 2007/0244552 A1 | 10/2007 | Salahieh |
| 2007/0288089 A1 | 12/2007 | Gurskis |

(56) References Cited

U.S. PATENT DOCUMENTS

| | | |
|---|---|---|
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson |
| 2008/0125859 A1 | 5/2008 | Salahieh |
| 2008/0188928 A1 | 8/2008 | Salahieh |
| 2008/0208328 A1 | 8/2008 | Antocci |
| 2008/0208332 A1 | 8/2008 | Lamphere |
| 2008/0221672 A1 | 9/2008 | Lamphere |
| 2008/0234814 A1 | 9/2008 | Salahieh |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz |
| 2009/0030512 A1 | 1/2009 | Thielen |
| 2009/0054969 A1 | 2/2009 | Salahieh |
| 2009/0076598 A1 | 3/2009 | Salahieh |
| 2009/0093877 A1 | 4/2009 | Keidar et al. |
| 2009/0171456 A1 | 7/2009 | Kveen |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh |
| 2009/0299462 A1 | 12/2009 | Fawzi |
| 2010/0036479 A1 | 2/2010 | Hill et al. |
| 2010/0049313 A1 | 2/2010 | Alon |
| 2010/0082089 A1 | 4/2010 | Quadri et al. |
| 2010/0094399 A1 | 4/2010 | Dorn et al. |
| 2010/0121434 A1 | 5/2010 | Paul |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0280495 A1 | 11/2010 | Paul |
| 2010/0298931 A1 | 11/2010 | Quadri et al. |
| 2011/0257735 A1 | 10/2011 | Salahieh et al. |
| 2011/0264196 A1 | 10/2011 | Savage et al. |
| 2011/0288634 A1 | 11/2011 | Tuval et al. |
| 2011/0295363 A1 | 12/2011 | Girard et al. |
| 2012/0022642 A1 | 1/2012 | Haug et al. |
| 2012/0029627 A1 | 2/2012 | Salahieh et al. |
| 2012/0041550 A1 | 2/2012 | Salahieh et al. |
| 2012/0053683 A1 | 3/2012 | Salahieh et al. |
| 2012/0089224 A1 | 4/2012 | Haug et al. |
| 2012/0179244 A1 | 7/2012 | Schankereli et al. |
| 2012/0303113 A1 | 11/2012 | Benichou et al. |
| 2012/0330409 A1 | 12/2012 | Haug et al. |
| 2013/0018457 A1 | 1/2013 | Gregg et al. |
| 2013/0030520 A1 | 1/2013 | Lee et al. |
| 2013/0079867 A1 | 3/2013 | Hoffman et al. |
| 2013/0079869 A1 | 3/2013 | Straubinger et al. |
| 2013/0096664 A1 | 4/2013 | Goetz et al. |
| 2013/0138207 A1 | 5/2013 | Quadri et al. |
| 2013/0158656 A1 | 6/2013 | Sutton et al. |
| 2013/0184813 A1 | 7/2013 | Quadri et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |
| 2015/0012085 A1 | 1/2015 | Salahieh et al. |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| EP | 0103546 | 5/1988 |
| EP | 0144167 | 11/1989 |
| EP | 0409929 B1 | 4/1997 |
| EP | 0850607 | 7/1998 |
| EP | 0597967 | 12/1999 |
| EP | 1000590 A1 | 5/2000 |
| EP | 1057459 | 12/2000 |
| EP | 1057460 | 12/2000 |
| EP | 1088529 | 4/2001 |
| EP | 0937439 B1 | 9/2003 |
| EP | 1340473 | 9/2003 |
| EP | 1356793 | 10/2003 |
| EP | 1042045 B1 | 5/2004 |
| EP | 0819013 | 6/2004 |
| EP | 1435879 | 7/2004 |
| EP | 1439800 | 7/2004 |
| EP | 1589902 | 8/2004 |
| EP | 1605871 | 9/2004 |
| EP | 1472996 | 11/2004 |
| EP | 1229864 B1 | 4/2005 |
| EP | 1430853 | 6/2005 |
| EP | 1059894 B1 | 7/2005 |
| EP | 1551274 A2 | 7/2005 |
| EP | 1551336 A1 | 7/2005 |
| EP | 1078610 B1 | 8/2005 |
| EP | 1562515 A1 | 8/2005 |
| EP | 1570809 | 9/2005 |
| EP | 1576937 A2 | 9/2005 |
| EP | 1582178 A2 | 10/2005 |
| EP | 1582179 A2 | 10/2005 |
| EP | 1469797 | 11/2005 |
| EP | 1600121 A1 | 11/2005 |
| EP | 1156757 B1 | 12/2005 |
| EP | 1616531 | 1/2006 |
| FR | 2788217 | 7/2000 |
| SU | 1271508 | 11/1986 |
| SU | 1371700 | 2/1988 |
| WO | 2056023 | 3/1981 |
| WO | 9217118 | 10/1992 |
| WO | 9301768 | 2/1993 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 96/24306 A1 | 8/1996 |
| WO | 96/40012 | 12/1996 |
| WO | 9829057 | 7/1998 |
| WO | WO 98/36790 | 8/1998 |
| WO | WO 98/50103 A1 | 11/1998 |
| WO | WO 98/57599 A2 | 12/1998 |
| WO | 9933414 | 7/1999 |
| WO | 9940964 | 8/1999 |
| WO | 9947075 | 9/1999 |
| WO | WO 99/44542 A2 | 9/1999 |
| WO | 9117720 | 11/1999 |
| WO | WO 00/09059 | 2/2000 |
| WO | 0041652 | 7/2000 |
| WO | 0044311 | 8/2000 |
| WO | 0045874 | 8/2000 |
| WO | 0047139 | 8/2000 |
| WO | WO 00/44308 | 8/2000 |
| WO | WO 00/44313 | 8/2000 |
| WO | WO 00/49970 A1 | 8/2000 |
| WO | WO 00/67661 | 11/2000 |
| WO | WO 01/05331 | 1/2001 |
| WO | WO 01/08596 A1 | 2/2001 |
| WO | WO 01/10320 A1 | 2/2001 |
| WO | WO 01/10343 A1 | 2/2001 |
| WO | 0135870 | 5/2001 |
| WO | WO 01/35870 | 5/2001 |
| WO | 0149213 | 7/2001 |
| WO | 0154625 | 8/2001 |
| WO | 0162189 | 8/2001 |
| WO | 0164137 | 9/2001 |
| WO | WO 01/64137 | 9/2001 |
| WO | 0176510 | 10/2001 |
| WO | 0197715 | 12/2001 |
| WO | 0241789 | 5/2002 |

(56) References Cited

FOREIGN PATENT DOCUMENTS

| | | |
|---|---|---|
| WO | WO 02/36048 | 5/2002 |
| WO | WO 02/41789 A2 | 5/2002 |
| WO | 0243620 | 6/2002 |
| WO | 0247575 | 6/2002 |
| WO | 02056955 | 7/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO03/030776 A2 | 4/2003 |
| WO | 03047648 | 6/2003 |
| WO | 03094793 | 11/2003 |
| WO | WO 03/015851 | 11/2003 |
| WO | WO03/094797 A1 | 11/2003 |
| WO | 2004006803 | 1/2004 |
| WO | 2004006804 | 1/2004 |
| WO | 2004014256 | 2/2004 |
| WO | 2004019811 | 3/2004 |
| WO | 2004019817 | 3/2004 |
| WO | 2004021922 | 3/2004 |
| WO | 2004023980 | 3/2004 |
| WO | WO 2004/019811 | 3/2004 |
| WO | WO 2004/023980 | 3/2004 |
| WO | 2004026117 | 4/2004 |
| WO | 2004043293 | 5/2004 |
| WO | WO 2004/041126 | 5/2004 |
| WO | WO 2004/047681 | 6/2004 |
| WO | 2004058106 | 7/2004 |
| WO | 2398245 | 8/2004 |
| WO | 2004066876 | 8/2004 |
| WO | 2004082536 | 9/2004 |
| WO | 2004089250 | 10/2004 |
| WO | 2004089253 | 10/2004 |
| WO | 2004093728 | 11/2004 |
| WO | 2004105651 | 12/2004 |
| WO | 2005002466 | 1/2005 |
| WO | 2005004753 | 1/2005 |
| WO | 2005009285 | 2/2005 |
| WO | 2005011534 | 2/2005 |
| WO | 2005011535 | 2/2005 |
| WO | 2005023155 | 3/2005 |
| WO | 2005027790 | 3/2005 |
| WO | 2005046528 | 5/2005 |
| WO | 2005046529 | 5/2005 |
| WO | 2005048883 | 6/2005 |
| WO | 2005062980 | 7/2005 |
| WO | 2005065585 | 7/2005 |
| WO | WO 2005/084595 A1 | 9/2005 |
| WO | WO 2005/087140 A1 | 9/2005 |
| WO | 2005096993 | 10/2005 |
| WO | 2006005015 | 1/2006 |
| WO | 2006009690 | 1/2006 |
| WO | 2006027499 | 3/2006 |
| WO | 2006093795 | 9/2006 |
| WO | 2006138391 | 12/2006 |
| WO | 2007009117 | 1/2007 |
| WO | 2007033093 | 3/2007 |
| WO | 2007035471 | 3/2007 |
| WO | 2007044285 | 4/2007 |
| WO | 2007053243 | 5/2007 |
| WO | 2007058847 | 5/2007 |
| WO | 2007092354 | 8/2007 |
| WO | 2007097983 | 8/2007 |
| WO | 2010042950 | 4/2010 |
| WO | 2010/098857 A1 | 9/2010 |

OTHER PUBLICATIONS

Atwood, A. et al., "Insertion of Heart Valves by Catheterization". The Capstone Design Course Report. MIME 1501-1502. Technical Design Report. Northeastern University. Nov. 5, 2007, pp. 1-93.
Oct. 24, 2011, Supplemental Search Report from EP Patent office, EP Application No. 05758878.2.
"A Matter of Size, Triennial Review of the National Nanotechnology Initiative," 2006, v-13, The National Academies Press, Washington, DC htt://www.nap.edu/catalog/11752.html.
Aug. 19, 2011, Supplemental Search Report from EP Patent Office, EP Application No. 04813777.2.
Aug. 19, 2011, Supplemental Search Report from EP Patent Office, EP Application No. 04815634.3.
Cunanan, Crystal, M., M.S., et al., "Tissue Characterization and Calcification Potential of Commercial Bioprosthetic Heart Valves," 2001, S417-21, Elsevier Science Inc.
EP Search Report mailed Aug. 10, 2011 for EP Application No. 06824992.9.
H.R. Cunliffe, et al., "Glutaraldehyde Inactivation of Exotic Animal Viruses in Swine Heart Tissue," May 1979, 1044-1046, vol. 37, No. 5., Applied and Environmental Microbiology, Greenport, New York.
Heart Valve Materials—Bovine (cow), Equine & Porcine Pericardium, Maverick Biosciences PTY. LTD, Jan. 7, 2011, http:ll www.maverickbio.com/biological-medical-device-materials. php?htm.
Hourihan, Maribeth, et al., "Transcatheter Umbrella Closure of Valvular and Paravalvular Leaks," Nov. 15, 1992, 1371-7, vol. 20, No. 6, JACC, Boston Massachusetts.
J.C. Laborde, "Percutaneous implantation of the corevalve aortic valve prosthesis for patients presenting high risk for surgical valve replacement," 2006, 472-474, EuroIntervention.
Levy, Charles, M.D., "Mycobacterium Chelonei Infection of Porcine Heart Valves," Sep. 22, 1977, vol. 297, No. 12, The New England Journal of Medicine, Washington, D.C.
Pericardial Heart Valves, Edwards Lifesciences, Cardiovascular Surgery FAQ, 11114/2010, http://www.edwards.com/ products/ cardiovascularsurgeryfaq.htm.
Sochman, J. et al., "Percutaneous Transcatheter Aortic Disc Valve Prosthesis Implantation: A Feasibility Study".Cardiovasc. Intervent. Radiol (2000) 23, 384-388.
Stassano, Paolo, "Mid-term results of the valve-on-valve technique for bioprosthetic failure," 2000, 453-457, European Journal of Cardio-thoracic Surgery.
Stuart, M., "In Heart Valves, A Brave, New Non-Surgical World." Start-Up (2004) 9-17.
Topol, Eric J., M.D., "Percutaneous Expandable Prosthetic Valves," Textbook of Interventional Cardiology, 1994, 1268-1276, vol. 2, W.B. Saunders Company, Philadelphia.
Vahanian, A. et al., "Percutaneous Approaches to Valvular Disease." Circulation (2004) 109, 1572-1579.
Van Herwerden, L.A. et al., "Percutaneous Valve Implantation: back to the furture?"Euro Heart J. (2002) 23:18, 1415-1416.
Zhou, J. Q. et al., "Self-Expandable valve stent of large size: off-bypass implantation on pulmonary position". Eur. J. Cardiothorac (2003) 24, 212-216.
Paul et al.; U.S. Appl. No. 12/578,463 entitled "Medical Devices and Delivery Systems for Delivering Medical Devices," filed Oct. 13, 2009.
Paul et al.; U.S. Appl. No. 12/578,447 entitled "Medical Devices and Delivery Systems for Delivering Medical Devices," filed Oct. 13, 2009.
Haug et al.; U.S. Appl. No. 12/492,512 entitled "Everting Heart Valve," filed Jun. 26, 2009.
Salahieh, et al., U.S. Appl. No. 12/264,082 entitled "Repositionable heart valve and method," filed Nov. 3, 2008.
Salahieh, et al., U.S. Appl. No. 12/269,213 entitled "Everting heart valve," filed Nov. 12, 2008.
Salahieh, et al., U.S. Appl. No. 12/132,304 entitled "Low profile heart valve and delivery system," filed Jun. 3, 2008.
Haug et al.; U.S. Appl. No. 12/028,452 entitled "Methods and apparatus for endovascularly replacing a patient's heart valve," filed Feb. 8, 2008.
Haug, et al; U.S. Appl. No. 11/716,123, entitled "Methods and apparatus for endovascularly replacing a heart valve," filed Mar. 9, 2007 (SLG #10012-701.301).
Salahieh, et al; U.S. Appl. No. 11/706,549, entitled "Systems and Methods for Delivering a Medical Implant," filed Feb. 14, 2007 (SLG #10012-732.201).

(56) References Cited

OTHER PUBLICATIONS

Salahieh, et al; U.S. Appl. No. 11/732,906 entitled "Assessing the location and performance of replacement heart valves," filed Apr. 4, 2007 (SLG #10012-702.505).
Salahieh, et al., U.S. Appl. No. 11/531,980, "Externally expandable heart valve anchor and method," filed Sep. 14, 2006 SLG Ref 10012-703.301 (formerly 30207-703.301).
Salahieh, et al., U.S. Appl. No. 11/532,019, "Methods and apparatus for endovascularly replacing heart valve," filed Sep. 14, 2006 SLG Ref 10012-703.302 (formerly 30207-703.302).
Salahteh, et al., U.S. Appl. No. 11/275,912, entitled "Medical Implant Delivery and Deployment Tool," filed Feb. 2, 2006 (WSGR Reference No. 30207-722.501).
Salahieh, et al., U.S. Appl. No. 11/275,913, entitled "Two-Part Package for Medical Implant," filed Feb. 2, 2006 (WSGR Reference No. 30207-723.201).
Salahieh, et al., U.S. Appl. No. 11/314,183, entitled "Medical Device Delivery," filed Dec. 20, 2005 (WSGR Reference No. 30207-725.201).
Andersen, H.R. et al. "Transluminal implantation of artificial heart valves. Description of a new expandable aortic valve and initial results with implantation by catheter technique in closed chest pigs." *Euro. Heart J.* 1992; 13:704-708.
Atwood, A. et al. "Insertion of Heart Valves by Catheterization." Project Supervised by Prof. S. Muftu of Northeaster University 2001-2002: 36-40.
Bodnar, E. et al. Replacement Cardiac Valves—Chapter 13: Extinct cardiac valve prostheses. *Pergamon Publishing Corporation.* New York, 1991: 307-332.
Boudjemline, Y. et al. "Percutaneious implantation of a biological valve in the aorta to treat aortic valve insufficiency—a sheep study." *Med Sci. Monit.* 2002; vol. 8, No. 4: BR113-116.
Boudjemline, Y. et al. "Percutaneous implantation of a valve in the descending aorta in lambs." *Euro. Heart J.* 2002; 23: 1045-1049.
Boudjemline, Y. et al. "Percutaneous pulmonary valve replacement in a large right ventricular outflow tract: an experimental study." *Journal of the Americal College of Cardiology.* 2004; vol. 43(6): 1082-1087.
Boudjemline, Y. et al. "Percutaneous valve insertion: a new approach?" *J. of Thoracic and Cardio. Surg.* 2003; 125(3): 741-743.
Boudjemline, Y. et al. "Steps Toward Percutaneous Aortic Valve Replacement." *Circulation.* 2002; 105: 775-778.
Cribier, A. et al. "Early Experience with Percutaneous Transcatheter Implantation of Heart Valve Prosthesis for the Treatment of End-Stage Inoperable Patients with Calcific Aortic Stenosis." *J. of Am. Coll. of Cardio.* 2004; 43(4): 698-703.
Cribier, A., et al. "Percutaneous Transcatheter Implantation of an Aortic Valve Prosthesis for Calcific Aortic Stenosis: First Human Case Description." *Circulation.* 2002; 106: 3006-3008.
Cribier, A., et al. "Percutaneous Transcatheter Implantation of an Aortic Valve Prosthesis for Calcific Aortic Stenosis: First Human Case." *Percutaneous Valve Technologies, Inc.* 2002: 16 pages.
Ferrari, M. et al. "Percutaneous transvascular aortic valve replacement with self expanding stent-valve device." Poster from the presentation given at SMIT 2000, 12th International Conference. Sep. 5, 2000.

Hijazi, Z.M. "Transcatheter Valve Replacement: A New Era of Percutaneous Cardiac Intervention Begins." *J. of Am. College of Cardio.* 2004; 43(6): 1088-1089.
Huber, C.H. et al. "Do valved stents compromise coronary flow?" *European Jouranl of Cardiothoracic Surgery.* 2004; vol. 25: 754-759.
Knudsen, L. L. et al. "Catheter-implanted prosthetic heart valves." *Int'l J. of Art. Organs.* 1993; 16(5): 253-262.
Kort, S. et al. "Minimally invasive aortic valve replacement: Echocardiographic and clinical results." *Am. Heart J.* 2001; 142(3): 476-481.
Love, C. et al. "The Autogenous Tissue Heart Valve: Current Status." *Journal of Caridac Surgery.* 1991; 6(4): 499-507.
Lutter, G. et al. "Percutaneous aortic valve replacement: An experimental study. I. Studies on implantation." *J. of Thoracic and Cardio. Surg.* 2002; 123(4): 768-776.
Moulopoulos, S. D. et al. "Catheter-Mounted Aortic Valves." *Annals of Thoracic Surg.* 1971; 11(5): 423-430.
Paniagua, D. et al. "Percutaneous heart valve in the chronic in vitro testing model." *Circulation.* 2002; 106: e51-e52.
Paniagua, D. et al. Heart Watch (2004). *Texas Heart Institute.* Spring, 2004 Edition: 8 pages.
Pavcnik, D. et al. "Percutaneous bioprosthetic venous valve: A long-term study in sheep." *J. of Vascular Surg.* 2002; 35(3): 598-603.
Phillips, S. J. at al. "A Temporary Catheter-Tip Aortic Valve: Hemodynamic Effects on Experimental Acute Aortic Insufficiency." *Annals of Thoracic Surg.* 1976; 21(2): 134-136.
Sochman, J. et al. "Percutaneous Transcatheter Aortic Disc Valve Prosthesis Implantation: A Feasibility Study." *Cardiovasc. Intervent. Radiol.* 2000; 23: 384-388.
Stuart, M. "In Heart Valves, A Brave, New Non-Surgical World." *Start-Up.* 2004: 9-17.
Vahanian, A. et al. "Percutaneous Approaches to Valvular Disease." *Circulation.* 2004; 109: 1572-1579.
Van Herwerden, L. A. et al., "Percutaneous valve implantation: back to the future?" *Euro. Heart J.* 2002; 23(18): 1415-1416.
Zhou, J. Q. et al. "Self-expandable valved stent of large size: off-bypass implantation in pulmonary position." *Eur. J. Cardiothorac.* 2003; 24: 212-216.
Fawzi, et al., U.S. Appl. No. 11/155,309, entitled "Apparatus and methods for intravascular embolic protection," filed Jun. 16, 2005 (WSGR Reference No. 30207-719.201).
Salahieh, et al., U.S. Appl. No. 11/232,441, entitled "Methods and apparatus for endovascular heart valve replacement comprising tissue grasping elements," filed Sep. 20, 2005 (WSGR Reference No. 30207-702.503).
Salahieh, et al., U.S. Appl. No. 11/232,444, entitled "Methods and apparatus for endovascular heart valve replacement comprising tissue grasping elements," filed Sep. 20, 2005 (WSGR Reference No. 30207-702.504).
Salahieh, et al., U.S. Appl. No. 11/274,889, entitled "Medical implant deployment tool," filed Jun. 16, 2005 (WSGR Reference No. 30207-718.201).

\* cited by examiner

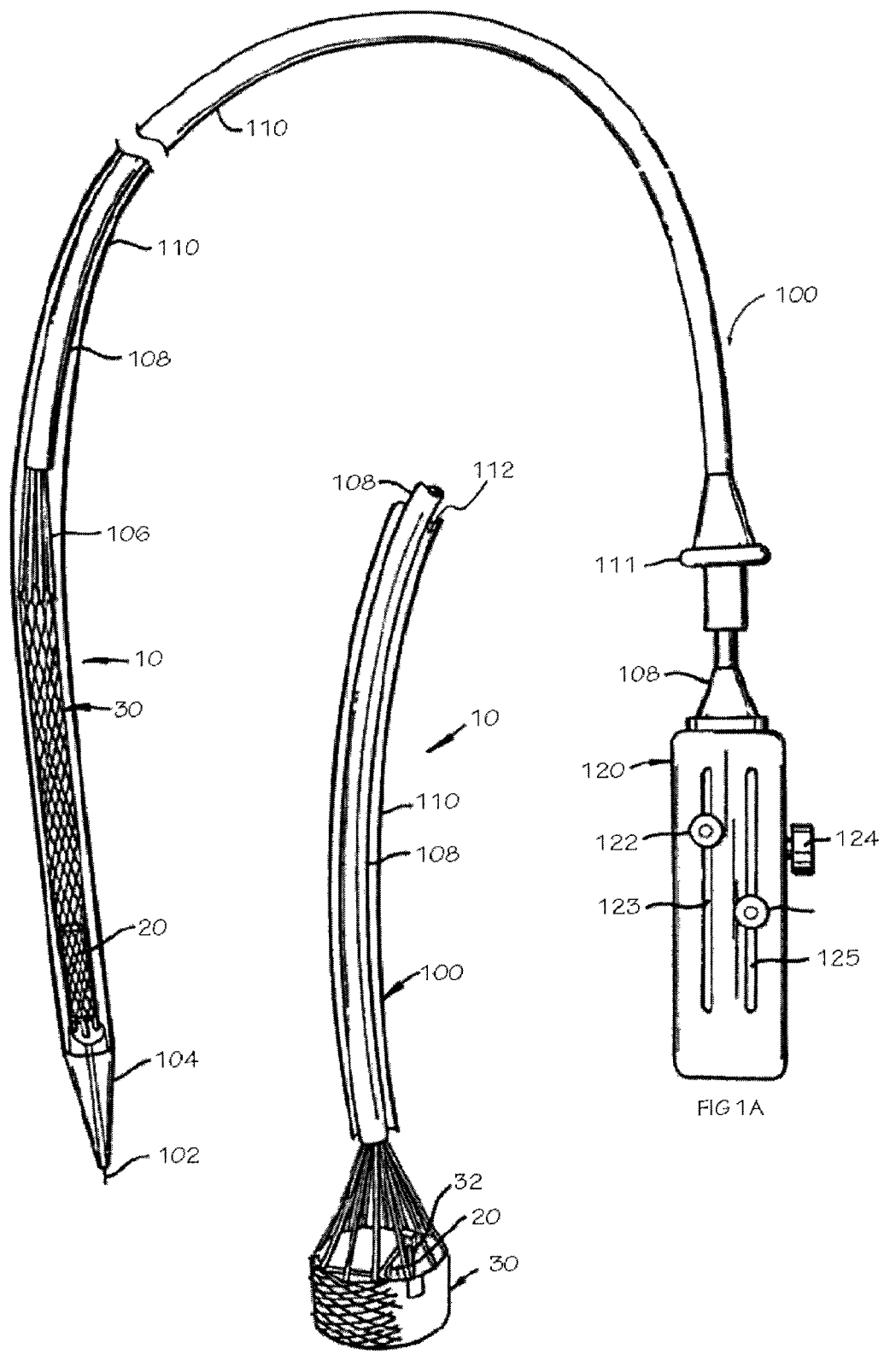

LOADED   RELEASED

METHODS AND APPARATUS FOR PERFORMING VALVULOPLASTY

CROSS-REFERENCE TO RELATED APPLICATIONS

This application is a continuation of U.S. application Ser. No. 11/314,969, filed Dec. 20, 2005, which claims the benefit of priority of U.S. Provisional Application Ser. No. 60/724, 455, filed Oct. 6, 2005, and is a continuation-in-part of application Ser. No. 10/982,692, filed Nov. 5, 2004, now U.S. Pat. No. 7,824,442, which is a continuation-in-part of application Ser. No. 10/746,120, filed Dec. 23, 2003, now abandoned, all of which are incorporated herein by reference in their entirety and to which we claim priority under 35 USC §§119 and 120.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to methods and apparatus for performing valvuloplasty. More particularly, the present invention relates to methods and apparatus for performing valvuloplasty as an adjunct to percutaneous transcatheter heart valve replacement.

BACKGROUND OF THE INVENTION

Failing heart valves can become calcified and stenotic. Valvuloplasty is a procedure that can break calcification and open up heart valves. With the advent of percutaneous transcatheter heart valve replacement ("PTVR"), the importance of valvuloplasty devices and procedures may increase, since a valvuloplasty procedure may be required to facilitate the proper placement and/or expansion of a percutaneously delivered valve. Use of valvuloplasty in connection with PTVR is expected to present unique challenges not previously addressed or accounted for by the valvuloplasty prior art.

One problem associated with prior art balloon-based valvuloplasty devices is that the balloon may conform to the profile of the stenosed native valve, as opposed to forcing the stenosed valve to conform to a desired predetermined shape or profile of the balloon. Furthermore, some balloon-based valvuloplasty devices completely occlude the native valve and thereby stop the flow of blood during the valvuloplasty procedure. This severely limits the amount of time over which the procedure may be practiced and brings additional risks to the already debilitated patient, thereby limiting the patient population on whom the procedure may be performed.

Pedersen US 2005/0090846 is a balloon-based device that incorporates a valve within the balloon in order to maintain blood flow during the valvuloplasty procedure. In such a device, the balloon may require a relatively large cross-sectional area in order to generate the substantial radial pressure against the native valve necessary to perform the procedure, thereby increasing its profile and reducing the patient population in which the device may be utilized. As such, a balloon-based valvuloplasty device that incorporates a valve may only partially overcome the problem of flow occlusion during valvuloplasty, since its use may be limited by size constraints.

Another problem associated with prior art balloon-based valvuloplasty devices is the tendency of the valvuloplasty balloon to slip out of the stenotic area during the valvuloplasty procedure. Such slippage may, for example, arise as a result of the pressures exerted on the device by blood ejected from the beating heart, or as a function of how the valvuloplasty device inflates. A number of device designs have been conceived to try to reduce or eliminate slippage. Some of these designs make use of a shaped balloon in which a necked-in region is intended to interface with the stenosed region of the native valve (see, for example, PCT Publication No. WO 99/15223 to Cardeon Corporation, published Apr. 1, 1999). However, use of a valvuloplasty device incorporating a necked-in region requires precise placement of the valvuloplasty balloon prior to inflation and may not adequately dilate the target region. Other designs make use of an "ordered inflation", wherein the balloon sequentially inflates, for example, with the distal end of the balloon beginning to inflate first, followed by inflation of the proximal end and final inflation of the center of the balloon positioned across the native valve. See, e.g., Owens et al. U.S. Pat. No. 4,986,830.

An alternative prior art valvuloplasty technique, described, for example, in U.S. Pat. No. 6,932,838 to Schwartz et al., utilizes a number of "ribs" which, when constrained in such a way as to decrease the distance between their proximal and distal ends, "bulge" radially outward and apply radially outward-directed forces to the stenotic native valve. These devices suffer from a number of shortcomings. The minimal number of point contacts associated with the small number of ribs is expected to localize forces, thereby increasing the risk of localized tissue failure, e.g., perforation or dissection. Such devices also may be less efficient at transmitting the force provided by the medical practitioner into the radially- and outwardly-directed forces necessary for expansion of the native stenosed valve, as compared to traditional balloon valvuloplasty devices. Furthermore, these devices may require precise placement both axially and rotationally relative to the stenotic native valve.

In view of the drawbacks associated with previously known methods and apparatus for performing valvuloplasty, it would be desirable to provide methods and apparatus that overcome those drawbacks. It also would be desirable to provide methods and apparatus for performing valvuloplasty that address the unique challenges associated with using such methods and apparatus as adjuncts to percutaneous transcatheter heart valve replacement.

SUMMARY OF THE INVENTION

One aspect of the invention provides an apparatus for performing valvuloplasty. The apparatus includes an expandable braid valvuloplasty device; and a delivery system configured for percutaneous delivery, expansion and retrieval of the braid valvuloplasty device at a valvuloplasty site to perform a valvuloplasty procedure. In some embodiments, the apparatus may include a valve configured to regulate blood flow during the valvuloplasty procedure. In some embodiments, the apparatus may include one or more measurement elements for monitoring the valvuloplasty procedure.

Another aspect of the invention provides a method for performing valvuloplasty, the method including the steps of percutaneously delivering an expandable braid valvuloplasty device to a valvuloplasty site within a patient, and temporarily expanding the expandable braid valvuloplasty device to perform the valvuloplasty. In some embodiments, the method may include regulating blood flow in a vicinity of the valvuloplasty site during the valvuloplasty. In some embodiments, the method may include monitoring at least one characteristic of the expandable braid valvuloplasty device during the valvuloplasty.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A and 1B are side views, partially in section, of valvuloplasty apparatus in accordance with the present invention;

DETAILED DESCRIPTION OF THE INVENTION

Figure 2A:
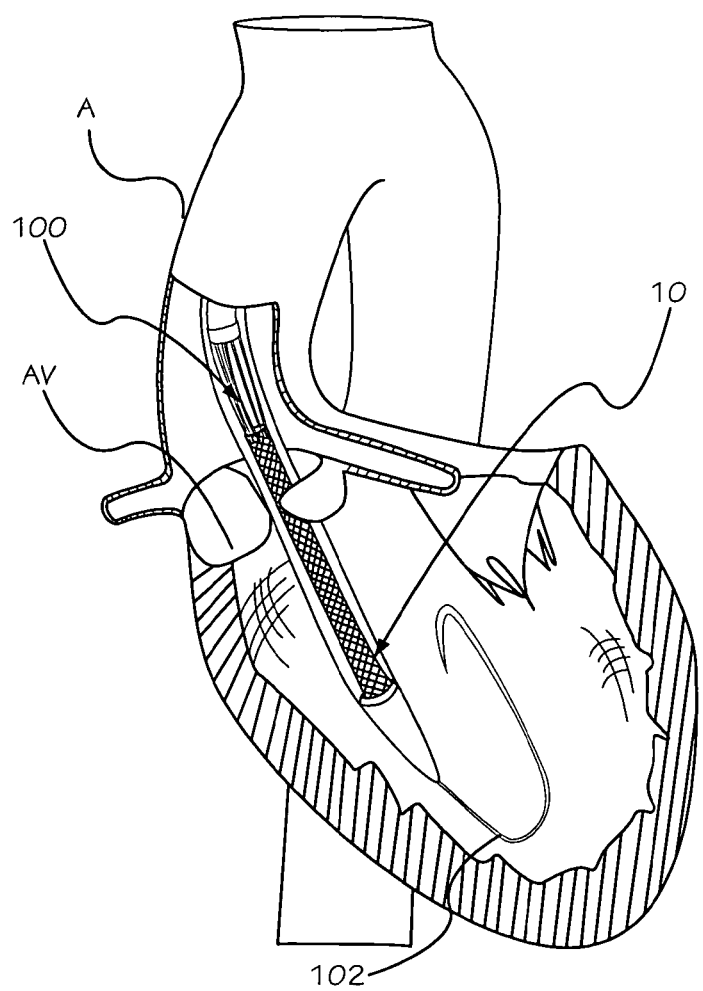
FIGS. 2A-2G are side views, partially in section, illustrating a method of using the apparatus of FIG. 1 to perform valvuloplasty.
Figure 2B:
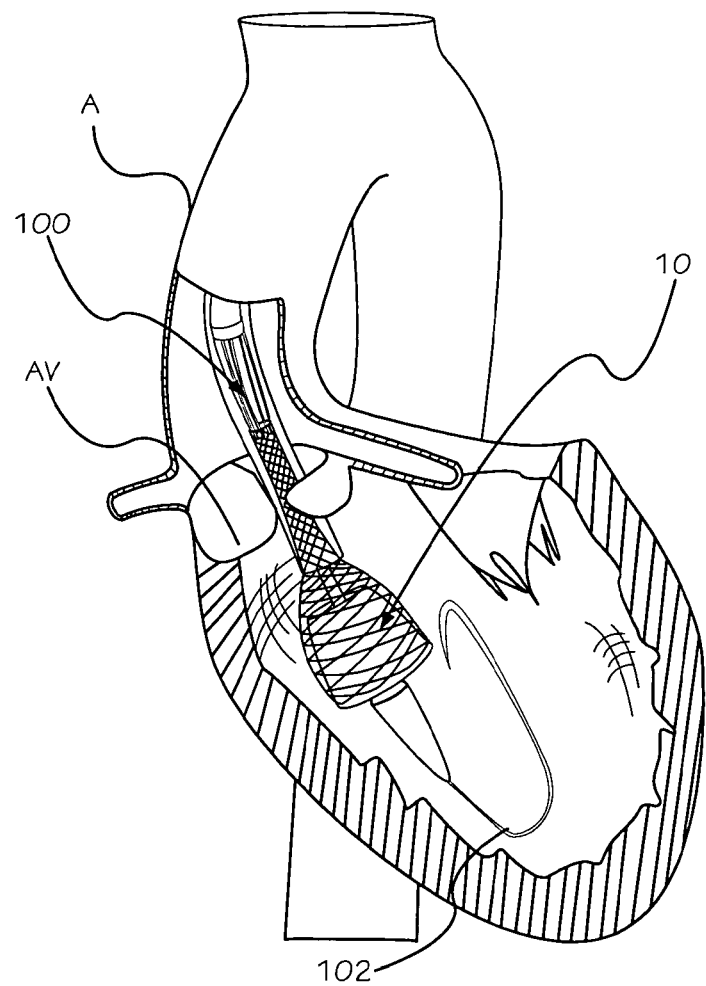
Figure 2C:
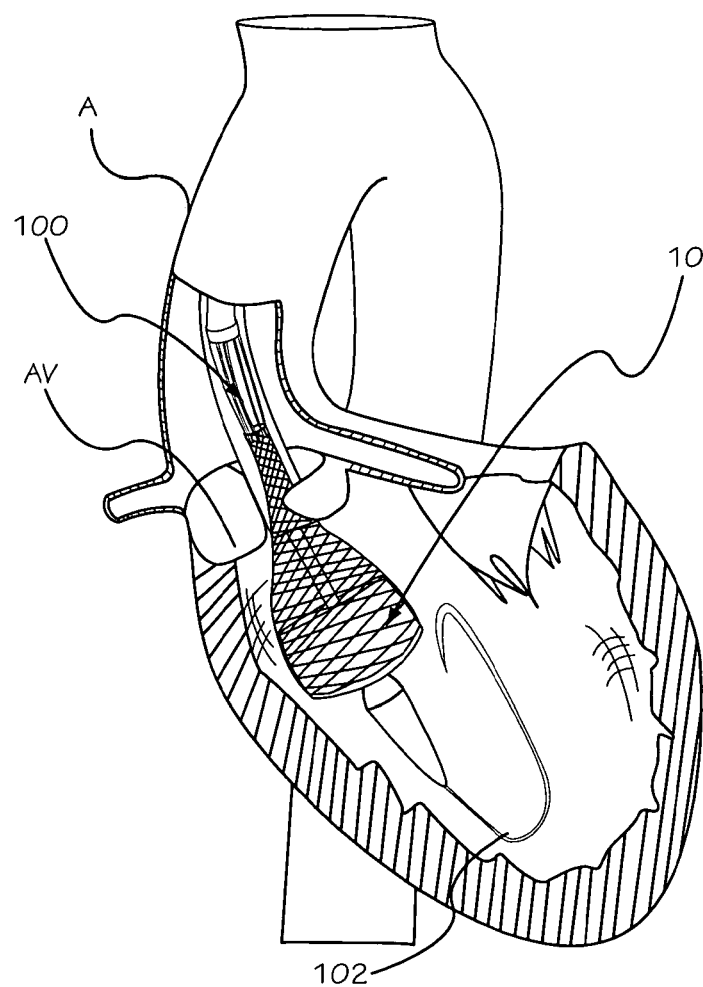
Figure 2D:
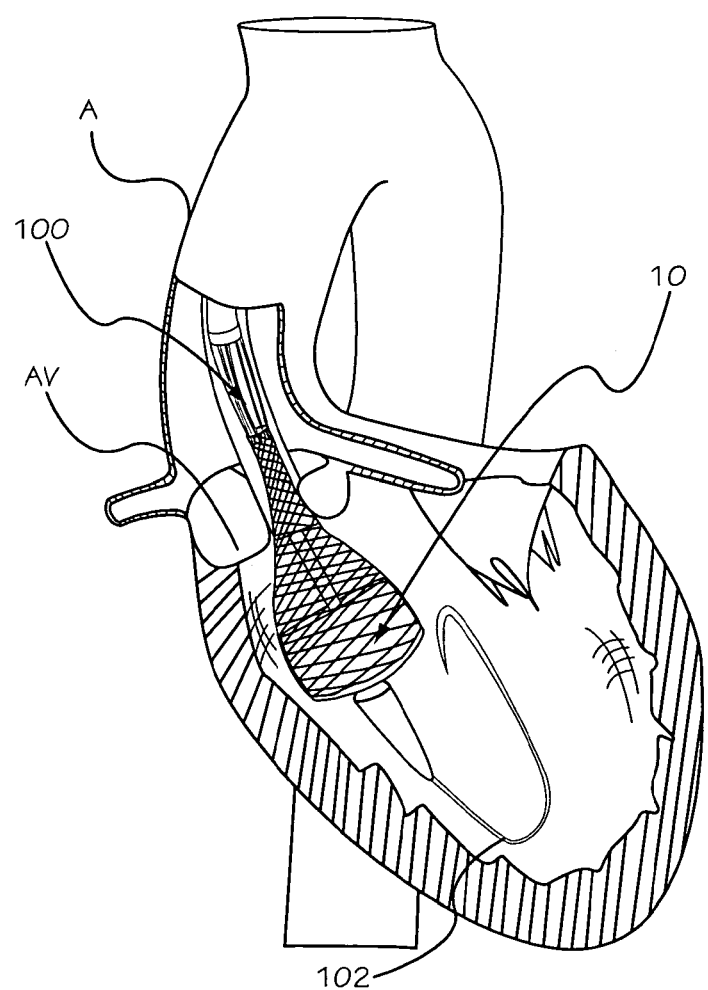

While preferred embodiments of the present invention are shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention relates to methods and apparatus for performing valvuloplasty. More particularly, the present invention relates to methods and apparatus for performing valvuloplasty as an adjunct to percutaneous transcatheter heart valve replacement ("PTVR"). Such use in connection with PTVR is expected to present unique challenges not previously addressed or accounted for by the prior art. For example, the medical practitioner may require additional feedback from the device when performing the valvuloplasty procedure.

An important consideration when performing PTVR is correctly sizing the valve implant to be used in the procedure. Characterization of valve size may not be derived easily from standard visualization information generally available to a physician at the time of valve implantation, e.g., from fluoroscopic imaging of the native valve. Furthermore, known procedures which could provide such information may be prohibitively costly, time-consuming and/or invasive.

Even if proper sizing information were derivable from standard visualization information, such visualization information typically would provide no information on the stiffness of the native valve system either pre- or post-valvuloplasty. An expanded PTVR implant may rely, at least to some extent, on counter forces provided by the surrounding tissue for proper anchoring and sealing function. Thus, the stiffness of the native valve system in the area of the implant may provide key information to the practitioner useful, for example, in characterization of proper implant size and/or implant stiffness. As such, a valvuloplasty system designed to provide information on appropriate PTVR implant radial expansion forces and/or PTVR implant size would provide significant utility to the PTVR medical practitioner and patient.

With reference to FIG. 1, a first embodiment of a valvuloplasty apparatus in accordance with the present invention is described. Versions of this embodiment may also be used as a PTVR implant. Further details of this embodiment are described in Ser. No. 10/746,120, filed Dec. 23, 2003, and Ser. No. 10/982,692, filed Nov. 5, 2004.

As illustrated by FIG. 1, valvuloplasty apparatus 10 includes an expandable braid 30 and an optional valve 20. Apparatus 10 may be collapsed for delivery within a delivery system 100, as in FIG. 1A. In this embodiment, delivery system 100 illustratively includes a guidewire 102 and a nosecone 104. Braid actuation elements 106 extending from a multi-lumen shaft 108 connect apparatus 10 to the delivery system and may be used to actuate apparatus 10, as described below. An external sheath 110 is positioned over the shaft 108, and a control handle 120 connects to shaft 108 at its proximal end. A proximal handle 111 moves sheath 110 with respect to handle 120 and shaft 108. As shown in FIG. 1A, apparatus 10 is collapsed for delivery with lumen 112 of external sheath 110 distal of multi-lumen shaft 108.

In the embodiment shown in FIG. 1, some of the actuation elements 106 are substantially stiff fingers extending between the distal end of shaft 108 and the proximal end of braid 30, and some of the actuation elements are control wires (e.g., strands of suture, or metal or polymer wires) extending from actuators 122, 124 and/or 126 in control handle 120 to the proximal ends of posts 32 attached to the distal end of braid 30 via, e.g., one or more lumens of the multi-lumen shaft 108. Alternatively, the control wires may connect directly to the distal end of braid 30. Braid actuation elements 106 may be connected directly to the valvuloplasty braid 30 in a manner that allows at least limited rotation between the braid and the actuation elements during expansion of the braid.

As illustrated in FIG. 1, apparatus 10 may also include a valve 20 within braid 30. Braid 30 can have closed ends (i.e., a continuous circumference) at either or both of its ends but preferably at least in its proximal end. As shown in FIG. 1B, optional valve 20 is coupled to the braid at posts 32. The optional posts can be attached to the braid's distal region, central region, or proximal region. Thus, optional posts 32 may function as a valve support and may be adapted to support the optional valve within the braid. In the embodiment shown, there are three posts, corresponding to the valve's three commissure attachments. Optional valve 20 can be composed of a metal, a synthetic material and/or may be derived from animal tissue. Valve 20 may be used to regulate blood flow during the valvuloplasty procedure. In embodiments in which the device is used as a PTVR implant, valve 20 is the replacement heart valve.

In some embodiments, braid 30 is collapsible and/or expandable and is formed from material such as Nitinol®, cobalt-chromium steel or stainless steel wire. For example, braid 30 may be self-collapsing and/or self-expanding and made out of shape memory material, such as Nitinol®. A braid composed of shape memory material may self-expand to or toward its "at-rest" configuration after removal of an external constraint, such as sheath 110. This "at-rest" configuration of a braid can be, for example its expanded configuration, its collapsed configuration, or a partially expanded configuration (between the collapsed configuration and the expanded configuration). In some embodiments, a braid's at-rest configuration is between its collapsed configuration and its expanded configuration. Depending on the "at-rest" diameter of the braid and the diameter of the patient's anatomy at the chosen deployment location, the braid may or may not self-expand to come into contact with the diameter of the patient's anatomy at that location upon removal of an external constraint. Further details regarding the braid, valve and delivery system may be found in Ser. No. 10/746,120, filed Dec. 23, 2003, and Ser. No. 10/982,692, filed Nov. 5, 2004.

During a valvuloplasty procedure, braid 30 may be expanded to a fully deployed configuration from a partial deployed configuration (e.g., a self-expanded or at-rest configuration). In the embodiment shown in FIG. 1, the braid 30 is expanded actively, e.g., by actively foreshortening braid 30 during endovascular deployment. Active foreshortening is described in more detail in U.S. patent application Ser. No. 10/746,120. During active foreshortening, the distal region of braid 30 is pulled proximally via a proximally-directed force applied to posts 32 via, e.g., actuation control elements and/or control wires connected to the distal region of the braid. Actuation control elements engaged with the proximal end of braid 30 provide a distally-directed counter-force to the proximally directed force. The proximally- and distally-directed forces applied to the distal and proximal regions, respectively, of the braid foreshorten the braid and expand it radially.

In some embodiments, active foreshortening of the apparatus involves applying a proximally-directed force on a deployment system interface at the distal end of the braid, while maintaining the proximal end of the braid in the same location. In other embodiments, foreshortening of the apparatus involves applying a distally-directed force on proximal end of the braid (e.g., by applying a distally-directed force on the braid actuation elements) while maintaining the distal end of the braid in the some location. In still other embodiments, a distally-directed force is applied to the proximal end of the braid, while a proximally-directed force is applied to the distal end of the braid.

The actuation elements (e.g., fingers, tubes, posts, and/or control wires connecting to posts), such as braid actuation elements 106, are preferably adapted to expand radially as the braid expands radially and to contract radially as the braid contracts radially. Furthermore, proximally- or distally-directed forces applied by actuation elements on one end of the braid do not diametrically constrain the opposite end of the braid. In addition, when a proximally- or distally-directed force is applied on the braid, it is preferably applied without passing any portion of the actuation elements through a center opening of the optional valve. This arrangement enables the valve to operate during valvuloplasty The active expansion of the braid optionally may be assisted via inflation of a balloon catheter (not shown) reversibly disposed within apparatus 10, as described in previously incorporated U.S. patent application Ser. No. 10/746,120. However, expansion without use of a balloon catheter is preferred such that flow is never occluded during deployment.

With reference to FIG. 2, in conjunction with FIG. 1, apparatus 10 may be utilized to perform valvuloplasty, e.g., aortic valvuloplasty. Such valvuloplasty may be utilized as an adjunct to PTVR. As seen in FIG. 2A, apparatus 10 may be advanced in a retrograde fashion through aorta A over guidewire 102 and placed across a patient's stenosed aortic valve AV using well-known percutaneous techniques. During delivery, apparatus 10 is positioned in the reduced delivery configuration within delivery system 100, as described with respect to FIG. 1A. Once positioned across the stenosed valve, external constraint may be partially removed from apparatus 10, for example, by retracting proximal handle 111 of sheath 110 relative to control handle 120, thereby retracting sheath 110 relative to apparatus 10 (handle 111 is positioned external to the patient). As seen in FIG. 2B, braid 30 of apparatus 10 begins to self-expand to the at-rest configuration. As seen in FIGS. 2C and 2D, apparatus 10 may be repositioned via delivery system 100 until the partially expanded distal region of the apparatus contacts the valve annulus, thereby ensuring proper positioning prior to completion of the valvuloplasty procedure.

Figure 2E:
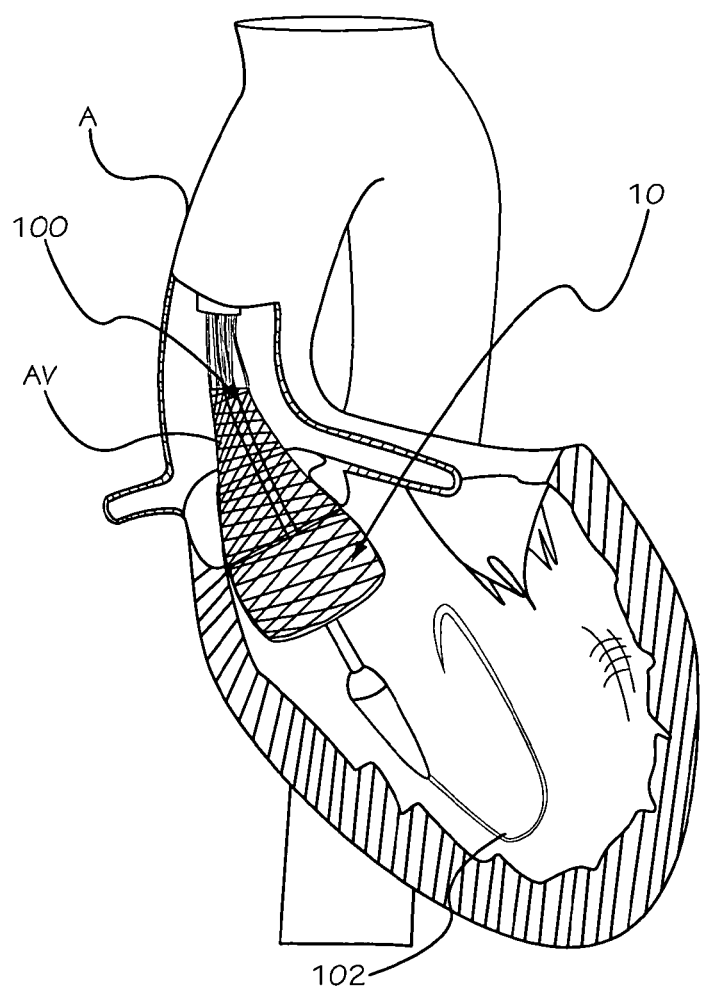
Figure 2F:
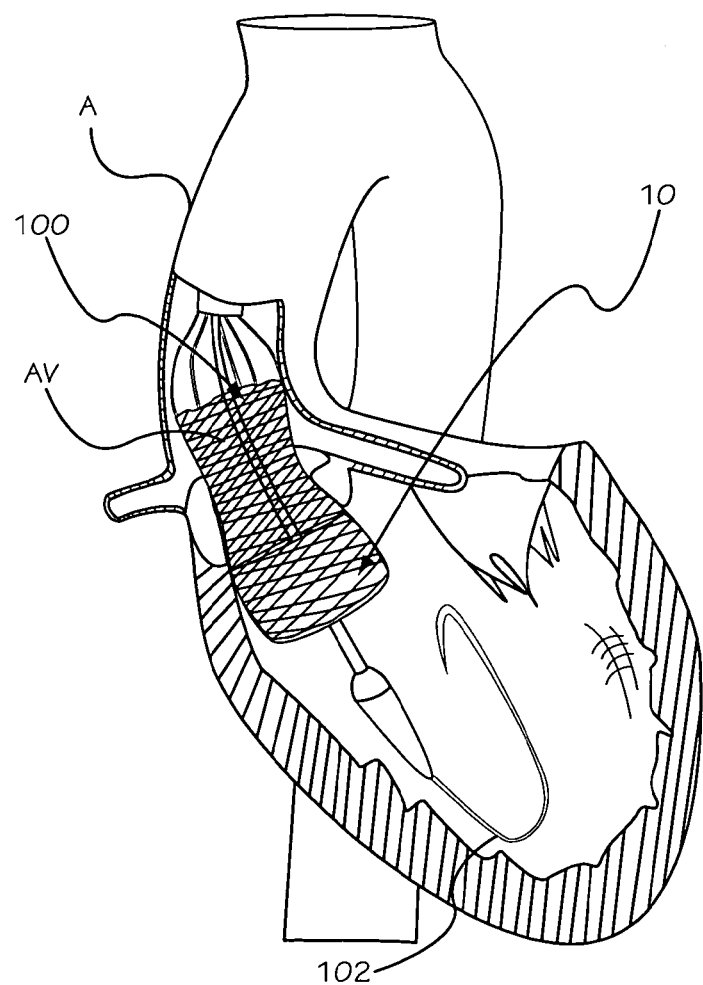
Figure 2G:
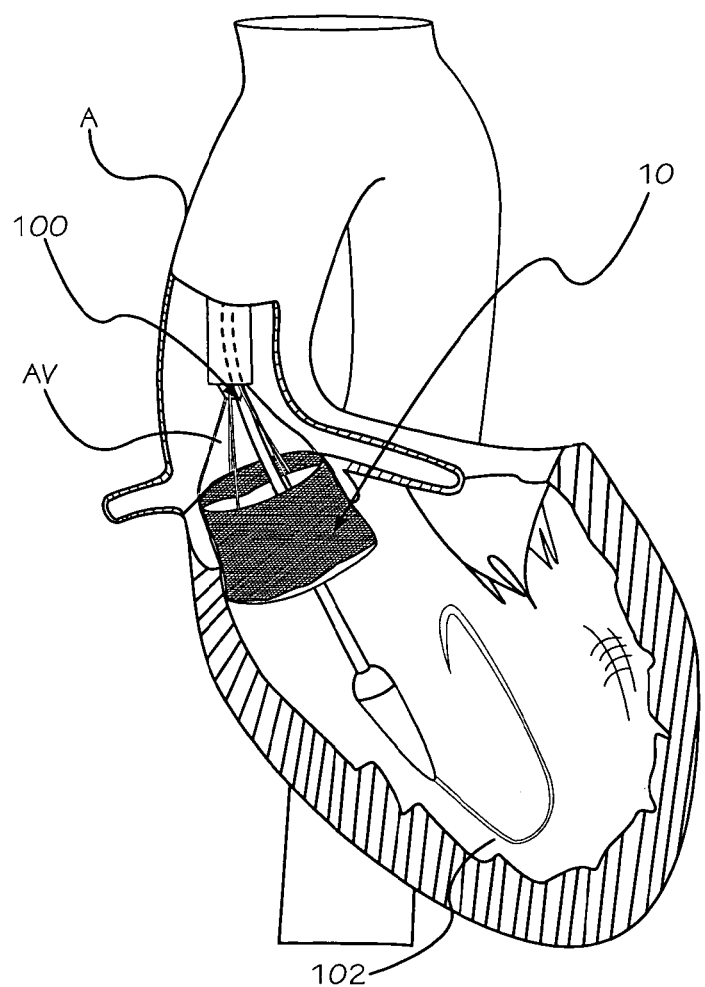

Once properly positioned, further retraction of sheath 110 fully removes the external constraint from apparatus 10 such that braid 30 assumes the at-rest configuration, as seen in FIGS. 2E and 2F. If present, optional valve 20 regulates blood flow through the device to ensure continuous perfusion of the patient both during deployment and retrieval of the apparatus, as well as during the actual valvuloplasty. Braid 30 then may be actively expanded, as described previously with respect to FIG. 1B, to the configuration of FIG. 2G, such that apparatus 10 applies a radially outward force to the native valve to perform the valvuloplasty and restore adequate flow through the patient's native valve. After completion of the valvuloplasty procedure, apparatus 10 may again be positioned within lumen 112 of sheath 110, for example by retracting multi-lumen shaft 108 and apparatus 10 relative to sheath 110. Braid actuation elements 106 provide a smooth transition that progressively collapses braid 30 and allows apparatus to be re-positioned within lumen 112 of sheath 110. Once fully collapsed, apparatus 10 and delivery system 100 may be removed from the patient.

Use of valvuloplasty apparatus 10 provides a number of advantages over known valvuloplasty devices. For example, use of braid 30 with optional valve 20 provides a large, unobstructed cross-sectional area for blood flow, while additionally providing valve function during the valvuloplasty procedure. Thus, the duration of the valvuloplasty procedure is not limited by loss of blood flow, as are procedures using fully occlusive or less occlusive, but valveless, valvuloplasty devices. This allows for more accurate and careful positioning of the device prior to and during the expansion process. Additionally, since blood flow is not stopped during the procedure, the procedure can be performed on patients who otherwise would be considered too ill to survive such a procedure.

Positioning of a valvuloplasty device should be affected only minimally by blood ejected from the beating heart. The relatively low occlusive cross-sectional area of apparatus 10 is expected to reduce forces exerted on the apparatus by blood passing through the aortic valve, thereby decreasing the force necessary to maintain the apparatus in place during the procedure, as compared to some known valvuloplasty devices. Thus, the likelihood that apparatus 10 will undesirably migrate during the procedure is expected to be reduced relative to current techniques. Furthermore, the relative roughness of the outer surface of braid 30, as compared to the roughness of traditional balloon valvuloplasty devices, also is expected to hold apparatus 10 in place and reduce the likelihood of slippage or migration during expansion of the apparatus.

As another advantage, apparatus 10 having braid 30, either with or without optional valve 20, is expected to provide a more uniform distension to the native stenosed valve than would be provided by either a balloon-based or a ribbed valvuloplasty device. Braid 30 is expected to force the native valve to conform to the shape of the foreshortened and radially expanded braid. Expansion of the braid is expected to impart a roughly cylindrical distension to the native valve tissue; when utilized as an adjunct to PTVR, this roughly cylindrical shape may approximate the shape of the intended implant.

Apparatus 10 also provides an inherent mechanical advantage to the transmission of force to the patient's native valve, as compared to ribbed valvuloplasty devices. Ribbed devices take a certain amount of force to bend, in addition to the force necessary to displace the native valve. Additionally, since the forces will be concentrated on a limited number of ribs, the stresses on these ribs will be concentrated thereby increasing the risk of failure. As another advantage, apparatus 10 is expected to have a relatively low profile delivery configuration, as compared to balloon valvuloplasty devices that include a central valve.

The manner in which apparatus 10 is deployed (i.e., active foreshortening of braid 30 via delivery system 100) may provide a medical practitioner with tactile or force feedback information indicative of calcific cracking along the calcified aortic valve. This is in contrast to inflation of a balloon valvuloplasty device, which may not provide the medical practitioner with adequate tactile information related to calcific cracking. Optionally, the force applied by the medical practitioner during deployment of apparatus 10, as well as the resultant foreshortening of braid 30, may be measured or monitored to provide a force vs. distension curve that is indicative of calcific cracking.

Figure 3:
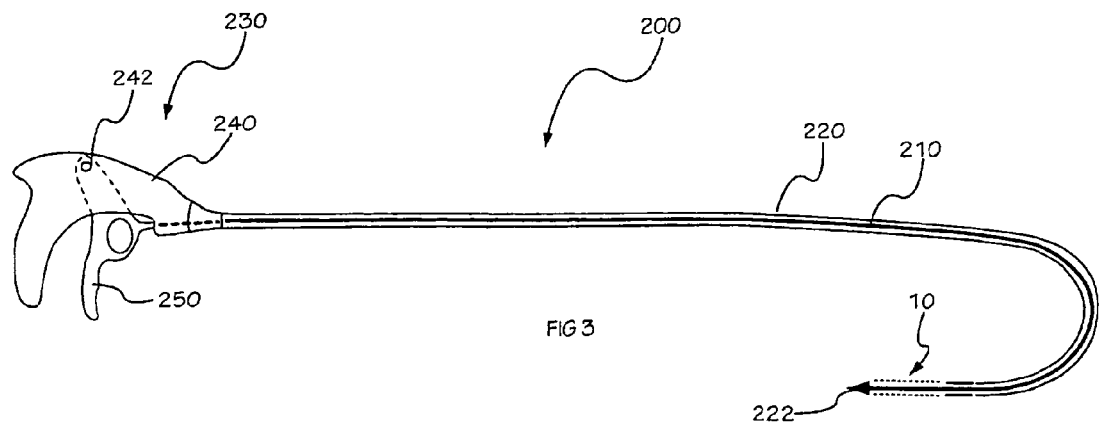
FIG. 3 is a schematic side view, partially in section, of an alternative delivery system for valvuloplasty apparatus of the present invention.

Given the short-term use of apparatus 10, simplified embodiments of the apparatus and/or of delivery system 100 may be provided. Some embodiments may, for example, incorporate control elements that pass through or are positioned within the center of the apparatus. Other embodiments may not include optional valve 20. With reference to FIG. 3, alternative delivery system 200 suitable for delivering, deploying and retrieving valvuloplasty apparatus 10 is described. In FIG. 3, apparatus 10 illustratively does not have a valve.

Delivery system 200 has an outer shaft 210 coupled to a proximal region of apparatus 10, as well as an inner shaft 220 that passes through the lumen of apparatus 10 and is coupled to a distal region of the apparatus. The inner and/or outer shafts may be connected directly to apparatus 10; alternatively, the inner and/or outer shafts may be connected to the apparatus through an intermediary element configured for radial expansion. Inner shaft 220 is coaxially disposed within outer shaft 210. The inner shaft terminates at nosecone 222 and preferably has a guidewire lumen (not shown). As in the embodiment of FIG. 1, delivery system 200 may also have an outer sheath (not shown) that constrains apparatus 10 in a reduced configuration during delivery and retrieval from a valvuloplasty site.

Delivery system 200 has a control assembly 230 having handle 240 and trigger 250. Trigger 250 is pivotably connected to handle 240 at pivot 242. Furthermore, trigger 250 is connected to inner shaft 220, while handle 240 is connected to outer shaft 210. As trigger 250 is pulled towards handle 240, inner shaft 210 is retracted proximally relative to outer shaft 220 such that the distance between the distal ends of the inner and outer shafts is decreased. Since the inner and outer shafts are respectively coupled to the distal and proximal regions of apparatus 10, braid 30 is foreshortened and increases in diameter. This diametric expansion may be utilized to perform valvuloplasty, as described previously.

Figures 4A, 4B:
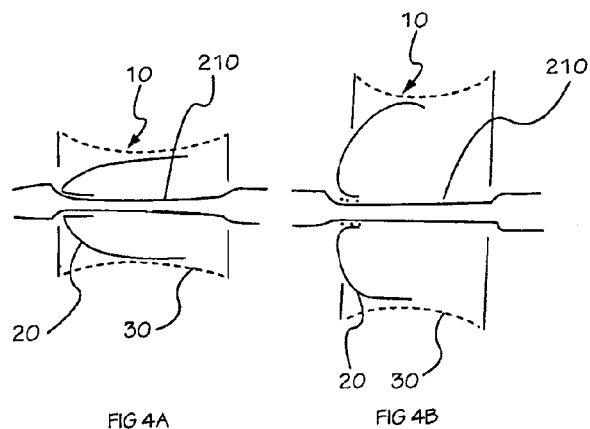
FIGS. 4A and 4B are schematic side-sectional detail views illustrating an embodiment of an optional valve utilized in combination with valvuloplasty apparatus of the present invention.

In embodiments of apparatus 10 that include the optional valve, the valve may comprise any of a variety of alternative valve designs. FIGS. 4 and 5 describe two such valve design embodiments. These embodiments are provided only for the sake of illustration and should in no way be construed as limiting; additional embodiments within the scope of the present invention will be apparent to those of skill in the art in view of this disclosure. In the embodiment of FIG. 4, valve 20 is centrally mounted within apparatus 10, e.g., is circumferentially coupled to inner shaft 210 of delivery system 200. FIG. 4A shows apparatus 10 in the at-rest configuration, while FIG. 4B shows the apparatus in the expanded deployed configuration for performing valvuloplasty. In either configuration, as well as during transition between the two configurations, blood flow may pass through apparatus 10 along the outer circumferential edge of valve 20 between the valve and braid 30.

Figures 5A, 5B:
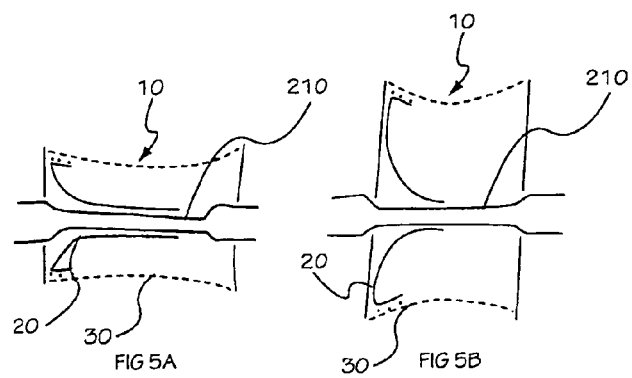
FIGS. 5A and 5B are schematic side-sectional detail views illustrating an alternative embodiment of an optional valve utilized in combination with valvuloplasty apparatus of the present invention.

In the embodiment of FIG. 5, valve 20 is mounted along the perimeter of apparatus 10, e.g., is coupled to braid 30, and has its opening in the middle of the apparatus. FIG. 5A shows apparatus 10 in the at-rest configuration, while FIG. 5B shows the apparatus in the expanded deployed configuration for performing valvuloplasty. In either configuration, as well as during transition between the two configurations, blood flow may pass through apparatus 10 through the center of valve 20. When valve 20 has a central opening as in FIG. 5, the valve may, for example, be configured as a single cusp, as multiple cusps, or as a spiral-shaped valve. In a preferred embodiment, the valve is a tricuspid valve. When spiral-shaped, the valve may, for example, comprise a strip of material that forms a helix on or along the inner diameter of the braid. The strip of material preferably is wide enough such that it is able to coapt against itself or against a central lumen or wire, such as a guidewire.

Figure 10A:
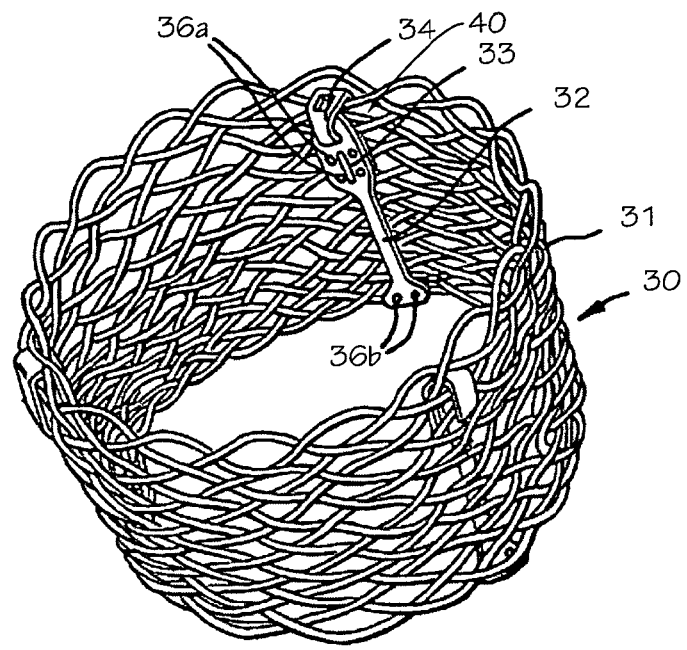
FIGS. 10A and 10B show details of a lockable expandable braid, with FIG. 10B showing the expandable braid supporting a valve.
Figure 10B:
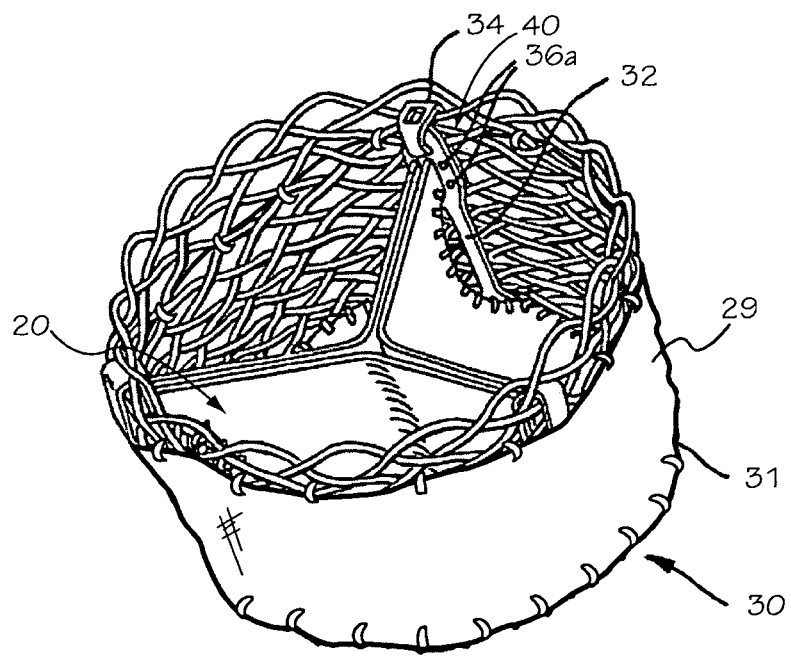

The apparatus optionally may have a seal that separates the interior of the apparatus from its exterior, e.g., that seals the openings in braid 30, such as seal 29 in FIG. 10B. The seal preferably is configured to expand with the braid. In use during valvuloplasty, the seal may facilitate sealing of the patient's native valve against the outside of the apparatus, while valve 20 functions within the interior of the apparatus. In this manner, the apparatus regulates blood flow during the valvuloplasty procedure, while reducing or eliminating uncontrolled leakage around the outside of the apparatus.

Figure 6:
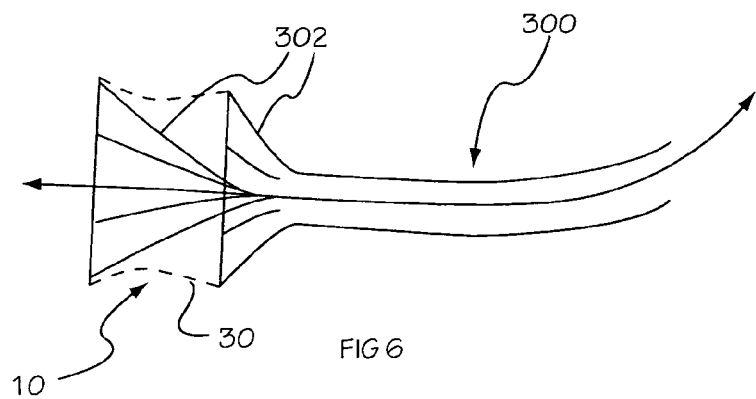
FIG. 6 is a schematic side-sectional detail view illustrating methods and apparatus for interfacing valvuloplasty apparatus of the present invention with a delivery system.
Figure 7:
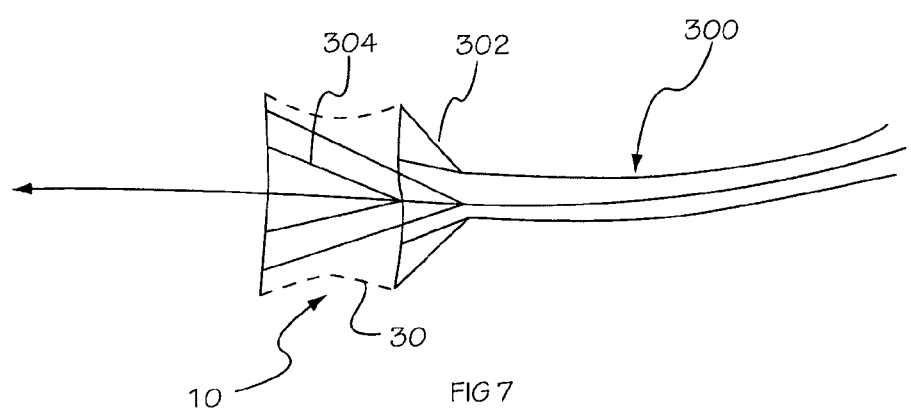
FIG. 7 is a schematic side-sectional detail view illustrating alternative methods and apparatus for interfacing valvuloplasty apparatus of the present invention with a delivery system.
Figure 8:
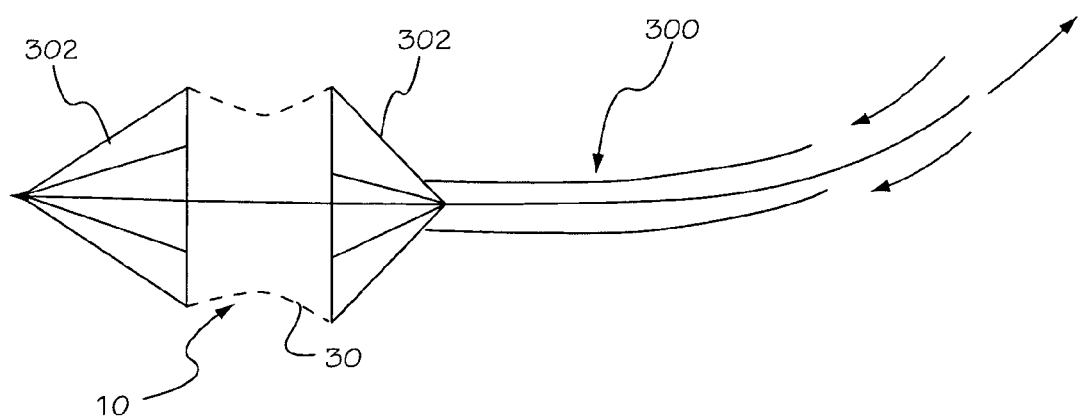
FIG. 8 is a schematic side-sectional detail view illustrating further alternative methods and apparatus for interfacing valvuloplasty apparatus of the present invention with a delivery system.

Referring now to FIGS. 6-8, the distal and proximal edges of braid 30 of apparatus 10 may be interfaced with a delivery system in a variety of ways in order to facilitate foreshortening, and thereby radial expansion, of the braid and of the apparatus. The exemplary embodiments of FIGS. 6-8 are provided only for the sake of illustration and should in no way be construed as limiting. Additional methods and apparatus within the scope of the present invention for interfacing braid 30 and/or apparatus 10 with a delivery system will be apparent to those of skill in the art in view of this disclosure.

In FIG. 6, delivery system 300 has a plurality of relatively stiff elements 302 coupled to both the distal and proximal ends of braid 30. In use, braid 30 may be foreshortened by applying a proximally directed force on the elements 302 coupled to the distal end of braid 30 and a distally directed force on the elements 302 coupled to the proximal end of braid 30. Elements 302 move radially with the braid during expansion and contraction of the braid.

In FIG. 7, stiff elements 302 are coupled to the proximal end of braid 30, while flexible control wires 304 are coupled to the distal end of the braid. Once again, braid 30 may be foreshortened by applying a proximally directed force on the control wires 304 and a distally directed force on the elements 302 coupled to the proximal end of braid 30.

In FIG. 8, delivery system 300 once again has relatively stiff elements 302 that are coupled to both the proximal and distal ends of braid 30. However, in the embodiment of FIG. 8, the distal elements 302 are placed in compression rather than in tension during foreshortening of braid 30 and expansion of apparatus 10.

When used, for example, as an adjunct to PTVR, apparatus 10 and/or the delivery system may provide information useful in preparing for a PTVR procedure. For example, the apparatus and/or the delivery system may provide information useful in characterizing the implant size suitable for a particular patient. The apparatus and/or the delivery system may incorporate elements for measuring diameter and/or for quantifying radial expansion forces at the location intended for the implant.

Measurement of the expanded diameter of braid 30 during the valvuloplasty procedure (and thereby measurement of, e.g., the proper size for a PTVR implant) may be derived from measurement of linear foreshortening of the braid. The relationship between diameter and linear foreshortening depends on the particular design of braid 30. However, the relationship can be well understood and or empirically characterized for any given design. In some embodiments, the relationship between the length of braid 30 and the diameter of the braid can be approximated by the relationship:

$$D = n(l^2 - K^2)^{1/2}/pi \tag{1}$$

here D is the diameter of the braid, l is the length of the braid, and K and n are constants specific to the design of the braid. In other embodiments K may also vary as a function of a braid characteristic, such as length.

When implanting a replacement heart valve, it may be important to ensure that the anchoring force—i.e., the force exerted by the replacement valve on the patient's tissue, which equals the force applied by the tissue on the native valve—is sufficient to prevent migration of the implant valve after implantation. The force that will be applied to the patient's tissue by a replacement valve and anchor expanded to a particular diameter may also be determined by the device of this invention. This combination of diameter and radial force at that diameter helps determine the size PTVR implant to use and/or the size to which an adjustably sized implant should be expanded. The radial expansion force applied to the patient's native valve and/or valve annulus during deployment of braid 30 (and thereby measurement of, e.g., the proper stiffness or expansion force for a PTVR implant) is related to the force exerted to foreshorten braid 30. As with the diameter measurement, the relationship between foreshortening force and radial expansion force depends on the particular design of the braid. However, for a given design, the relationship can be well understood and empirically characterized.

Figure 9:
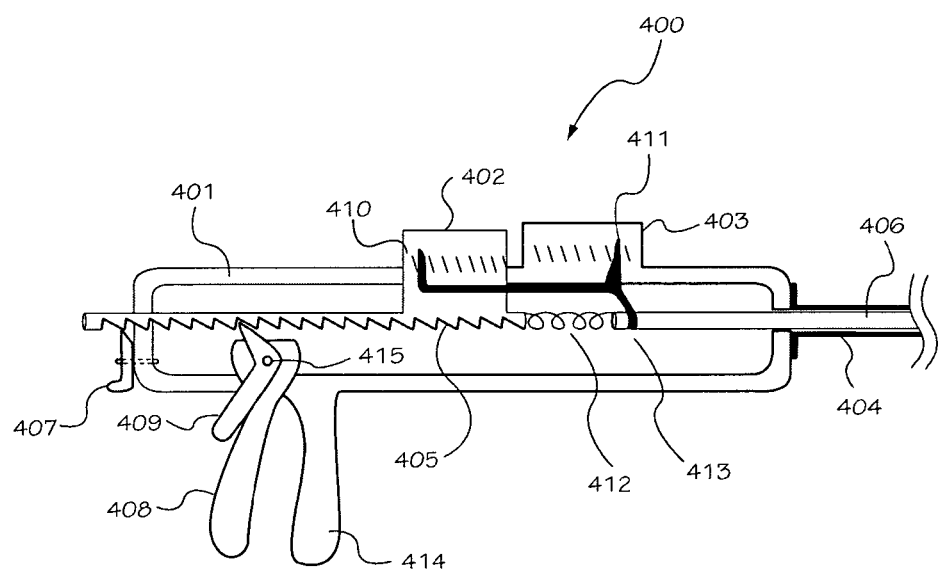
FIG. 9 is schematic side-sectional view of a control assembly for deploying and retrieving valvuloplasty apparatus of the present invention, the control assembly comprising measurement elements for determining information relevant to percutaneous transcatheter heart valve replacement.

Referring now to FIG. 9, control assembly 400 for deploying and retrieving valvuloplasty apparatus 10 is described. In this embodiment, the control assembly has measurement elements for determining information relevant to percutaneous transcatheter heart valve replacement. When used in combination with a delivery system, control assembly 400 is configured to measure the diameter of braid 30, as well as to determine the radial expansion force applied by the braid, during valvuloplasty with apparatus 10 at a location intended for subsequent placement of a PTVR implant. Control assembly 400 may be used in conjunction with any of the previously described delivery systems or with any other delivery system capable of delivering, deploying and retrieving apparatus 10. In FIG. 9, control assembly 400 illustratively is used in conjunction with delivery system 200 of FIG. 3, with control assembly 400 utilized in place of previously described control assembly 230. As described previously with respect to FIG. 3, the proximal region of apparatus 10 may be coupled to the distal end of outer shaft 220, while the distal region of the apparatus may be coupled to distal end of inner shaft 210.

When positioned at a valvuloplasty site, foreshortening of braid 30 of apparatus 10 may be achieved by squeezing trigger 408 such that it rotates about pivot 415 relative to handle 414. This proximally retracts ratchet element 405 relative to control assembly 400 via co-action between the ratchet and element 409 of the trigger. Element 409 is rotationally constrained around pivot 415 in the clockwise direction from its shown at-rest position. This movement retracts inner shaft 210 of delivery system 200 relative to outer shaft 220, thereby expanding apparatus 10. Spring-loaded tab 407 restrains ratchet 405 from slipping back to its original position in order to maintain the expansion of apparatus 10.

Control assembly 400 comprises a load-sensing capability and displacement-sensing capability. These two parameters provide information relating to the radial stiffness and to the diameter of the native valve or valve annulus. When ratchet element 405 is moved in the proximal direction, it transmits force through spring 412 to inner shaft 210 to move the inner shaft proximal relative to outer shaft 220. Diameter indicator needle 411, which is coupled to the proximal end of inner shaft 210, and displacement display 403 indicate the magnitude of displacement of inner shaft 210 relative to outer shaft 220. Since the outer shaft is coupled to the proximal region of apparatus 10 and the inner shaft is coupled to the distal region of the apparatus, this displacement measurement is indicative of the amount that braid 30 has foreshortened. As discussed previously, the diameter of apparatus 10 may be derived from measurement of linear foreshortening. In some embodiments, display 403 may be calibrated to the diameter of braid 30 or apparatus 10 such that indicator needle 411 provides a measurement of the diameter of apparatus 10. This diameter measurement may be used, e.g., to determine the size of a PTVR implant.

For measurement of radial expansion force, ratchet element 405, which is coupled to the proximal end of spring 412, may be read against load display 402. As spring 412 is urged proximally, load display 402 also moves in the proximal direction. The load or force necessary to sustain foreshortening of braid 30 and expansion of apparatus 10 is supported by spring element 412, which stretches in a characterizable amount in accordance with the magnitude of the load. For a standard spring this relationship is governed by Hooke's Law:

$$F=kx \qquad (2)$$

where F is the load or force supported by the spring, k is the spring constant (per se known), and x is the linear displacement or amount of "stretch" in the spring. This amount of "stretch" is indicated by the relative movement between load indicator needle 410, which is coupled to inner shaft 210 (illustratively via diameter indicator needle 411) and load display 402. The load display preferably is calibrated in load units, such that load indicator needle 410 provides a measurement of radial expansion forces. This measurement may be used, e.g., to select a PTVR implant of proper radial stiffness and diameter.

The above displacement-sensing capability also may be facilitated by a number of alternative means, including, but not limited to, linear encoders, rotary encoders in association with rotary to linear motion converters, linear variable displacement transformers ("LVDTs"), etc. Furthermore, the load sensing capability may be replaced by a load cell. In some of these alternate embodiments the load and displacement displays may be an electronic display which is capable of displaying outputs in real time. Such outputs may additionally be stored internally and or transmitted to other digital devices. Additionally, such displays may provide a graphic representation of both load and diameter.

In other embodiments, the replacement valve itself may be used to perform valvuloplasty prior to implantation. For example, the braid 30 and valve 20 of FIG. 1 may be expanded within the native valve through active foreshortening, as described above. The diameter and force measurement gauges of FIG. 9 may be employed to indicate the amount of expansion achieved and the amount of force applied to the native valve. After performing valvuloplasty, the apparatus may be left behind to function as a replacement heart valve instead of being removed from the patient as discussed above.

In some embodiments, the braid of the replacement valve apparatus may be locked in an expanded condition. One example of a locking braid is shown in FIG. 10. In this embodiment, openings are formed at the top end of posts 32. These openings engage buckles 34 when the braid is foreshortened to form a lock 40. Other locking anchor apparatus may be used, such as those described in Ser. No. 10/746,120, filed Dec. 23, 2003, and Ser. No. 10/982,692, filed Nov. 5, 2004.

Figures 11A, 11B:
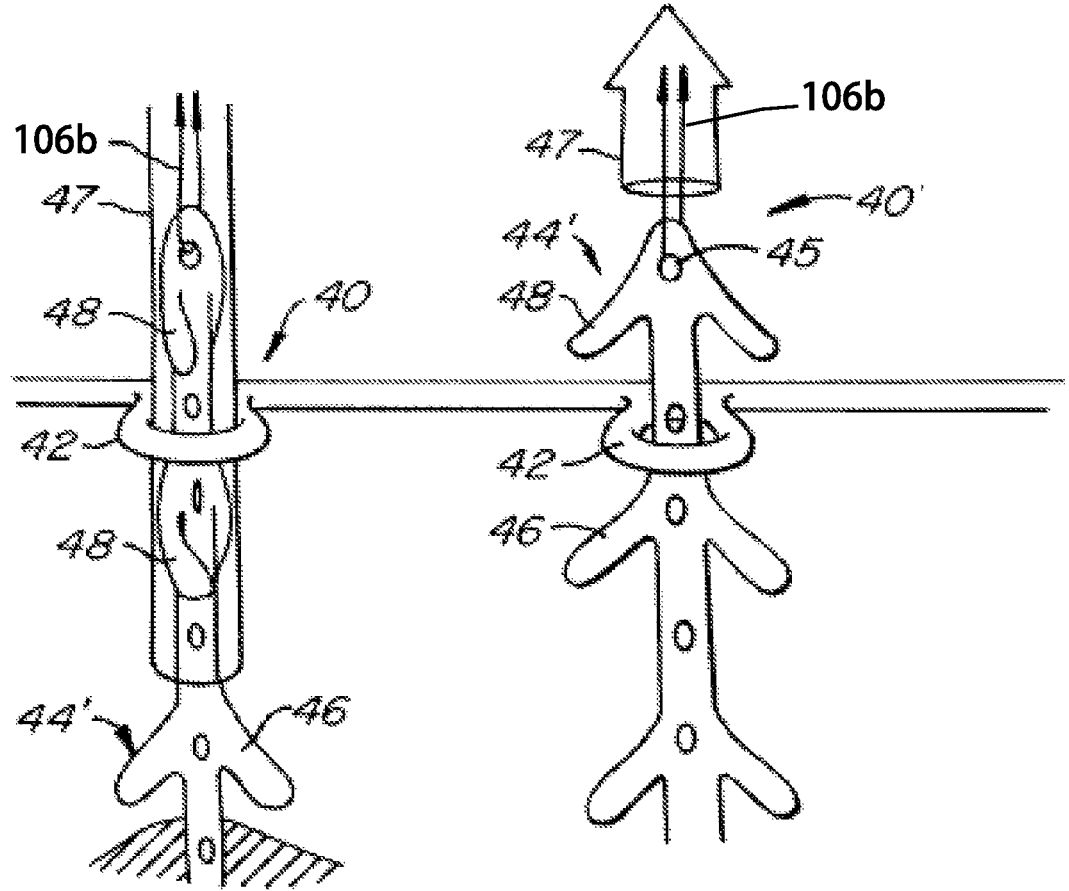
FIGS. 11A and 11B show details of a locking post for use with an expandable and lockable braid having multiple lock positions.

When a replacement valve apparatus with a locking anchor is used to perform valvuloplasty, it may be desirable to use an anchor that can be locked in multiple expanded diameters. For example, when the desired amount of expansion and expansion force has been achieved, the braided anchor may be locked in that diameter. One example of a post and buckle arrangement with multiple locking locations is shown in FIG. 11. In this embodiment, post 32 has multiple arrowhead shaped locking elements 46 with resilient or shape memory appendages 48 extending from them. In the unlocked configuration shown in FIG. 11A, an overtube 47 extending through buckle 42 prevents appendages from engaging buckle 42 as actuation element 106b pulls post 32 proximally into and through buckle 42. When overtube 47 is withdrawn (controlled, e.g., by an actuator on the proximal handle of the delivery system), appendages 48 move outward to engage buckle 42 and lock the anchor in its expanded configuration. Other multiple position anchor locks are described in Ser. No. 10/746,120, filed Dec. 23, 2003, and Ser. No. 10/982,692, filed Nov. 5, 2004.

Figures 12A, 12B:
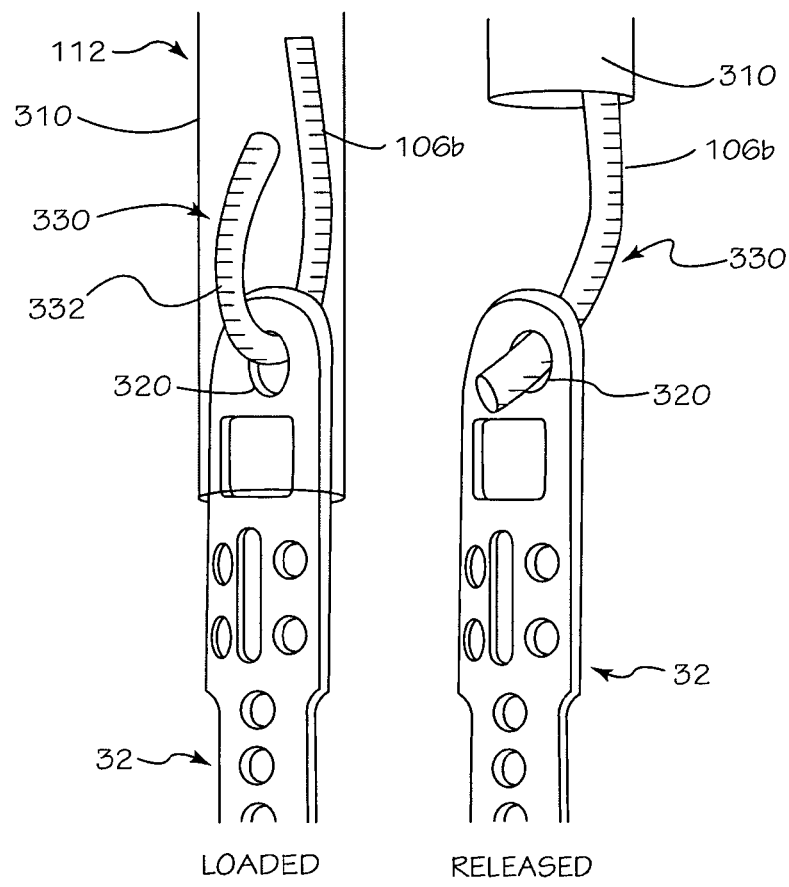
FIGS. 12A and 12B show details of one embodiment of an actuator element release mechanism for use with the invention.

Also, when a replacement valve and anchor is used to perform valvuloplasty, the delivery system must have some way of releasing the valve and anchor at the completion of the deployment and implantation procedure. FIG. 12 show an example of a release mechanism using an overtube 310 surrounding actuation element 106b. In FIG. 12A, the distal end 330 of actuation element 106b forms a hook 332 that passes through a hole 320 formed in the end of post 32. Withdrawal of overtube 310 (controlled, e.g., by an actuator on the proximal handle of the delivery system) permits actuation element 106b to straighten and withdraw from hole 320, as shown in FIG. 12B, thereby releasing post 32 from the delivery system. Similar release actuation mechanisms can be used for actuation elements controlling force delivered to the proximal end of the anchor. Other actuation element release mechanisms are described in Ser. No. 10/746,120, filed Dec. 23, 2003, and Ser. No. 10/982,692, filed Nov. 5, 2004.

What is claimed is:

1. A replacement heart valve comprising:
   an expandable anchor comprising a frame and a plurality of commissure attachment sites, the expandable anchor having a distal end, the frame defining a plurality of cell openings, and each of the commissure attachment sites defining at least one hole therethrough;
   a tricuspid valve attached to the expandable anchor at the commissure attachment sites;
   a seal extending along at least a portion of the frame, the seal being configured to cover at least some of the plurality of cell openings; and
   a plurality of anchor actuation elements;
   wherein the plurality of anchor actuation elements radially expand and foreshorten the expandable anchor to a deployed configuration by applying a proximally-directed force at the distal end of the expandable anchor and a distally-directed counter force at a proximal end of the expandable anchor.

2. The replacement heart valve of claim 1, wherein the commissure attachment sites further define a slot extending therethrough.

3. The replacement heart valve of claim 1, wherein the commissure attachment sites comprise posts.

4. The replacement heart valve of claim 1 further comprising a plurality of locking elements.

5. The replacement heart valve of claim 1, wherein the frame comprises a wire braid.

6. The replacement heart valve of claim 1, wherein the frame is formed from cobalt-chromium.

7. The replacement heart valve of claim 1, wherein the frame is formed from nickel-titanium.

8. The replacement heart valve of claim 1, wherein the frame is formed from stainless steel.

9. The replacement heart valve of claim 1, wherein the seal is disposed exteriorly to the frame.

10. The replacement heart valve of claim 1 further comprising a post and buckle, the post and buckle configured to engage one another and lock the frame in an expanded configuration.

11. The replacement heart valve of claim 1 further comprising a plurality of posts, each post having a plurality of locking elements defining appendages extending therefrom.

12. The replacement heart valve of claim 11 further comprising a plurality of buckles, wherein the appendages are configured to engage the buckles and lock the frame in an expanded configuration.

\* \* \* \* \*